(12) United States Patent
Haidekker et al.

(10) Patent No.: US 9,816,948 B2
(45) Date of Patent: Nov. 14, 2017

(54) COMPUTERIZED TOMOGRAPHY DETECTION OF MICROBIAL DAMAGE OF PLANT TISSUES

(71) Applicant: University of Georgia Research Foundation, Inc., Athens, GA (US)

(72) Inventors: Mark A. Haidekker, Athens, GA (US); Richard Speir, Loganville, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 258 days.

(21) Appl. No.: 14/689,104

(22) Filed: Apr. 17, 2015

(65) Prior Publication Data

US 2015/0300963 A1    Oct. 22, 2015

Related U.S. Application Data

(60) Provisional application No. 61/981,229, filed on Apr. 18, 2014.

(51) Int. Cl.
| | |
|---|---|
| G06K 9/00 | (2006.01) |
| G01N 23/04 | (2006.01) |
| G06T 7/00 | (2017.01) |
| G06T 11/00 | (2006.01) |
| G01N 33/02 | (2006.01) |

(52) U.S. Cl.
CPC ......... *G01N 23/046* (2013.01); *G01N 33/025* (2013.01); *G06T 7/0004* (2013.01); *G06T 11/008* (2013.01); *G01N 2223/618* (2013.01); *G06T 2207/10081* (2013.01); *G06T 2207/30128* (2013.01)

(58) Field of Classification Search
CPC ............... G01N 23/046; G01N 33/025; G01N 2223/618; G06T 7/0004; G06T 11/008; G06T 2207/10081; G06T 2207/30128
See application file for complete search history.

(56) References Cited

PUBLICATIONS

Li, Changying, et al. "Advancing Onion Postharvest Handling Efficiency and Sustainability by Multimodal Quality Sensing, Disease Control, and Waste Stream Management." HortScience. vol. 45. No. 8. 113 S West St, Ste 200, Alexandria, VA 22314-2851 USA: Amer Soc Horticultural Science, 2010.*

Haff, Ronald P., and Natsuko Toyofuku. "X-ray detection of defects and contaminants in the food industry." Sensing and Instrumentation for Food Quality and Safety 2.4 (2008): 262-273.*

(Continued)

*Primary Examiner* — Jonathan S Lee
(74) *Attorney, Agent, or Firm* — Thomas Horstemeyer, LLP

(57) ABSTRACT

The present disclosure encompasses embodiments of X-ray computed tomography-based methods for the detection of onion quality factors. Such methods are advantageous in detecting internal damage to onion bulbs due to bacterial and fungal rots and mechanical damage while also providing for the overall assessment of onion bulb quality and market value. Because CT images provide cross-sectional reconstructions of the subject under study, CT scans of onion bulbs can be used not only to detect damage from disease, but also cuts and bruises that increase an onion bulb's susceptibility to disease, and the presence of shoots or seed stems and overall shape of the bulbs.

3 Claims, 20 Drawing Sheets

(56) References Cited

PUBLICATIONS

Kotwaliwale, Nachiket, et al. "X-ray imaging methods for internal quality evaluation of agricultural produce." Journal of food science and technology 51.1 (2014): 1-15.*

E. G. Barcelon, S. Tojo, and K. Watanabe. X-ray computed tomography for internal quality evaluation of peaches. Journal of Agricultural Engineering Research, 73:323-330, 1999.

E. G. Barcelon, S. Tojo, and K. Watanabe. Relating X-ray absorption and some quality characteristics of mango fruit (*Mangifera indica* L.). Journal of Agriculture and Food Chemistry, 47:3822-3825, 1999.

J. K. Brecht, R. L. Shewfelt, J. C. Garner, and E. Tollner. Using X-ray computed tomography to nondestructively determine maturity of green tomatoes. HortScience, 26(1):45, 1991.

I. R. Donis-Gonzalez, D. E. Guyer, and A. Pease. Application of response surface methodology to systematically optimize image quality in computer tomography: A case study using fresh chestnuts (*Castanea* spp.). Computers and Electronics in Agriculture, 87:94-107, 2012.

J. H. Fromm, I. Sautter, D. Matthies, J. Kremer, P. Schumacher, and C. Ganter. Xylem water content and wood density in spruce and oak trees detected by high-resolution computed tomography. Plant Physiology, 127(2):416-425, Oct. 2001.

M. A. Haidekker. Shape analysis. In Advanced Biomedical Image Analysis, chapter 9, pp. 276-309. John Wiley and Sons, Hoboken, 2011.

M. A. Haidekker. Computed tomography. In Medical Imaging Technology, chapter 3, pp. 37-54. Springer, New York, 2013.

J. Lammertyn, T. Dresselaers, P. V. Hecke, P. Jancsok, M. Wevers, and B. Nicolai. MRI and CT study of spatial distribution of core breakdown in 'Conference' pears. Magnetic Resonance Imaging, 21:805-815,2003.

B. W. Maw, Y. Hung, E. W. Tollner, D. A. Smittle, and B. G. Mullinix. Detecting impact damage of sweet onions using muriatic acid and X-rays. Applied Engineering in Agriculture, 11(6):823-826, 1995.

I. Meglinski, C. Buranachai, and L. Terry. Plant photonics: Application of optical coherence tomography to monitor defects and rots in onion. Laser Physics Letters, 7(4):307-310, 2010.

M. R. P. Mosqueda, E. W. Tollner, G. E. Boyhan, and R. W. McClendon. Predicting the economics of X-ray inspection technology in sweet onion packinghouses using simulation modelling. Biosystems engineering, 105(1):139-147, 2010.

M. A. Shahin, E. W. Tollner, R. D. Gitaitis, D. R. Sumner, and B. W. Maw. Classification of sweet onions based on internal defects using image processing and neural network techniques. Transactions of the ASAE, 45(5):1613-1618, 2002.

L. Shepp and B. Logan. The fourier reconstruction of a head section. IEEE Trans Nucl. Sci, 21(3):21-43, 1974.

L. Sonego, R. Ben-Arie, J. Raynal, and J. Pech. Biochemical and physical evaluation of textural characteristics of nectarines exhibiting woolly breakdown: NMR imaging, X-ray computed tomography, and pectin composition. Postharvest Biology and Technology, 5:187-198, 1995.

E. W. Tollner, R. D. Gitaitis, K. W. Seebold, and B. W. Maw. Experiences with a food product X-ray inspection system for classifying onions. Applied Engineering in Agriculture, 21(5):907-912, 2005.

W. Wang, C. Li, E. W. Tollner, R. D. Gitaitis, and G. C. Rains. Shortwave infrared hyperspectral imaging for detecting sour skin (*Burkholderia cepacia*)-infected onions. Journal of Food Engineering, 109(1):38-48, 2012.

\* cited by examiner

COMPUTERIZED TOMOGRAPHY DETECTION OF MICROBIAL DAMAGE OF PLANT TISSUES

CROSS-REFERENCE TO RELATED APPLICATIONS

This application claims priority to U.S. Provisional Patent Application Ser. No. 61/981,229 entitled "CT TOMOGRAPHY DETECTION OF MICROBIAL DAMAGE OF PLANT TISSUES" and filed Apr. 18, 2014, the entirety of which is hereby incorporated by reference.

TECHNICAL FIELD

The present disclosure is generally related to methods of X-ray computed tomography scanning and image analysis techniques useful for the evaluation of the quality of agricultural products, and in particular onion bulbs.

BACKGROUND

Internal lesions caused by infectious pathogens, bruise damage, and bulb malformations are some features that can be detected by the methods proposed. Such an evaluation system could be used to ensure that only high-quality, healthy onions that have a high probability of storing for long periods enter controlled atmosphere storage. Additional quality factors such as bulb shape, consistency, and internal structure can be evaluated, leading to a premium onion grade that would command higher market prices, further increasing the value proposition of such a system to onion producers.

Worldwide, the onion (*Allium cepa*) is one of the most widely cultivated vegetable crops, second only to the tomato. Worldwide production of onions was 78.5 million metric tons in 2010. That same year, total harvested land area devoted to onion cultivation exceeded four million square hectares. In the United States, 2010 onion production was an estimated 3.72 million metric tons, with an aggregate farm gate value of approximately $1.15 billion.

The sweet yellow Granex varieties of onion grown in Georgia are collectively called Vidalia sweet onions and are a valuable economic commodity and have proven to be highly desirable to consumers due to their sweet and mild flavors. Vidalia onions are only harvested during a brief period of time every year, and the sweet flavor and high water content that makes them desirable to consumers also confer susceptibility to disease and decay, making it difficult to store them for long periods of time after harvest. Onion growers have attempted to extend the market availability of Vidalia onions by storing them in controlled atmosphere facilities, but disease outbreaks still frequently occur in these storage facilities, leading to substantial economic losses for the onion producers. Currently, onions entering storage are screened by human visual inspection for external signs of disease or damage that can increase disease susceptibility, but many onion diseases and defects manifest inside the bulb and can pass human inspection undetected.

Onions are biennial plants, growing vegetatively during the first year of life to maximize sugar production for storage in the bulb. As the plant matures, the leaves die and the plant enters a dormant stage until the next growing season when the plant produces flower stalks and seeds. These growth stages are regulated by the day-night cycle, and Granex varieties belong to a class of onion cultivars known as short-day (SD) onions due to the relatively short photoperiod (11-12 h) required to induce bulb formation in the plant. In the southern latitudes of the US, greenhouse-grown plantlets are typically transplanted to production fields in the late fall, where they grow vegetatively during the short winter days. As day length increases, plant growth shifts from leaf formation to bulb formation, and the onion bulbs are harvested from late April to early May when the bulbs reach a marketable size.

As harvest time approaches, the onion plant's leaves begin to break down, signaling that vegetative growth has stopped and that the plant is entering dormancy. When the onion leaves fall the bulbs can be harvested. A mechanical blade is run underneath the onion bulbs to sever the roots, and the bulbs are lifted out of the ground by the leaves and are left to cure for several days. Excessively hot or cold temperatures as well as heavy rains during the harvest and field curing of the onions can lead to increased incidence of bacterial and fungal rots that adversely affect their storability, leading to substantial losses for the growers. After field curing, the dead leaves are cut off, and bulbs are collected and transported to a sorting facility. There, human inspectors check for signs of disease or damage to the bulbs, and the bulbs are sorted by size. While human visual inspection can be useful in culling bulbs with obvious external defects, many bulbs may have internal damage or latent infections that are not detectable by eye.

While Vidalia onions remain popular with consumers because of their sweetness and lack of pungency, there are associated drawbacks. Laboratory tests of extracted onion flavor compounds have been shown to inhibit the growth of pathogenic fungi and bacteria. Vidalia onions are thought to be particularly susceptible to fungal and bacterial diseases because of their lack of these protective compounds. This increased susceptibility to disease has been a particular problem with regard to controlled atmosphere storage of onions for later sale. During particularly severe disease outbreaks, growers can lose more than 50% of their stored onions to postharvest diseases.

There are numerous pathogens and damage modes that can lead to diminished quality or complete loss of harvested onions, particularly as they are stored for increasing durations in controlled atmosphere facilities. Three of the most common post-harvest diseases affecting sweet onions are *Botrytis* fungal neck rot, *Burkholderia cepacia* bacterial rot, and *Pseudomonas viridiflava* bacterial rot.

SUMMARY

Briefly described, one aspect of the disclosure encompasses embodiments of a method of determining the quality of an onion bulb, said method comprising the steps of: (a) acquiring at least one CT image of an onion bulb; (b) adjusting the quality of the CT image to remove noise, enhance the contrast of the image and to enhance the edge of the image of the onion bulb; (c) identifying the outline of the onion bulb; (d) identifying the interior voids of the onion bulb; (e) obtaining a shape description of the onion bulb; (f) obtaining quantitative measurements of the interior voids of the onion bulb, wherein said measurements are of the relative sizes of the voids, the shapes of the voids, and the location of the voids relative to the internal layers of the onion bulb; (g) classifying the onion bulb with respect to at least one of: the quality of the onion as a marketable product, a disease type generating the voids in the onion bulb, and the extent of the progress of the disease within the onion bulb.

One aspect, therefore, of the disclosure encompasses embodiments of a method of determining the quality of an onion bulb, said method comprising the steps of: (a) acquiring at least one CT image of an onion bulb; (b) adjusting the quality of the CT image to remove noise, enhance the contrast of the image and to enhance the edge of the image of the onion bulb; (c) identifying the outline of the onion bulb; (d) identifying the interior voids of the onion bulb; (e) obtaining a shape description of the onion bulb; (f) obtaining quantitative measurements of the interior voids of the onion bulb, wherein said measurements are of the relative sizes of the voids, the shapes of the voids, and the location of the voids relative to the internal layers of the onion bulb; and (g) classifying the onion bulb with respect to at least one of: the quality of the onion as a marketable product, a disease type generating the voids in the onion bulb, and the extent of the progress of the disease within the onion bulb.

Another aspect of the disclosure encompasses embodiments of a non-transitory computer-readable medium embodying a program executable in at least one computing device, comprising code that: accesses a computed tomography (CT) image of an onion bulb; identifies an outline of the onion bulb in the CT image; identifies a plurality of interior voids of the onion bulb; generates a shape description of the onion bulb based at least in part on the plurality of interior voids, the outline of the onion bulb, or a combination thereof; generates a plurality of measurements for the interior voids of the onion bulb; and generates a classification for the onion bulb describing a condition of the onion bulb based at least in part on the plurality of measurements, the shape description, or a combination thereof.

Yet another aspect of the disclosure encompasses embodiments of a system comprising: at least one computing device; and an onion classification application executed in the at least one computing device, the onion classification application comprising logic that: accesses a computed tomography (CT) image of an onion bulb; identifies an outline of the onion bulb in the CT image; identifies a plurality of interior voids of the onion bulb; generates a shape description of the onion bulb based at least in part on the plurality of interior voids, the outline of the onion bulb, or a combination thereof; generates a plurality of measurements for the interior voids of the onion bulb; and generates a classification for the onion bulb describing a condition of the onion bulb based at least in part on the plurality of measurements, the shape description, or a combination thereof.

Yet another aspect of the disclosure encompasses embodiments of a computer-implemented method, comprising: accessing, by at least one computing device comprising at least one hardware processor, a computed tomography (CT) image of an onion bulb; identifying, by the at least one computing device, an outline of the onion bulb in the CT image; identifying, by the at least one computing device, a plurality of interior voids of the onion bulb; generating, by the at least one computing device, a shape description of the onion bulb based at least in part on the plurality of interior voids, the outline of the onion bulb, or a combination thereof; generating, by the at least one computing device, a plurality of measurements for the interior voids of the onion bulb; and generating, by the at least one computing device, a classification for the onion bulb describing a condition of the onion bulb based at least in part on the plurality of measurements, the shape description, or a combination thereof.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
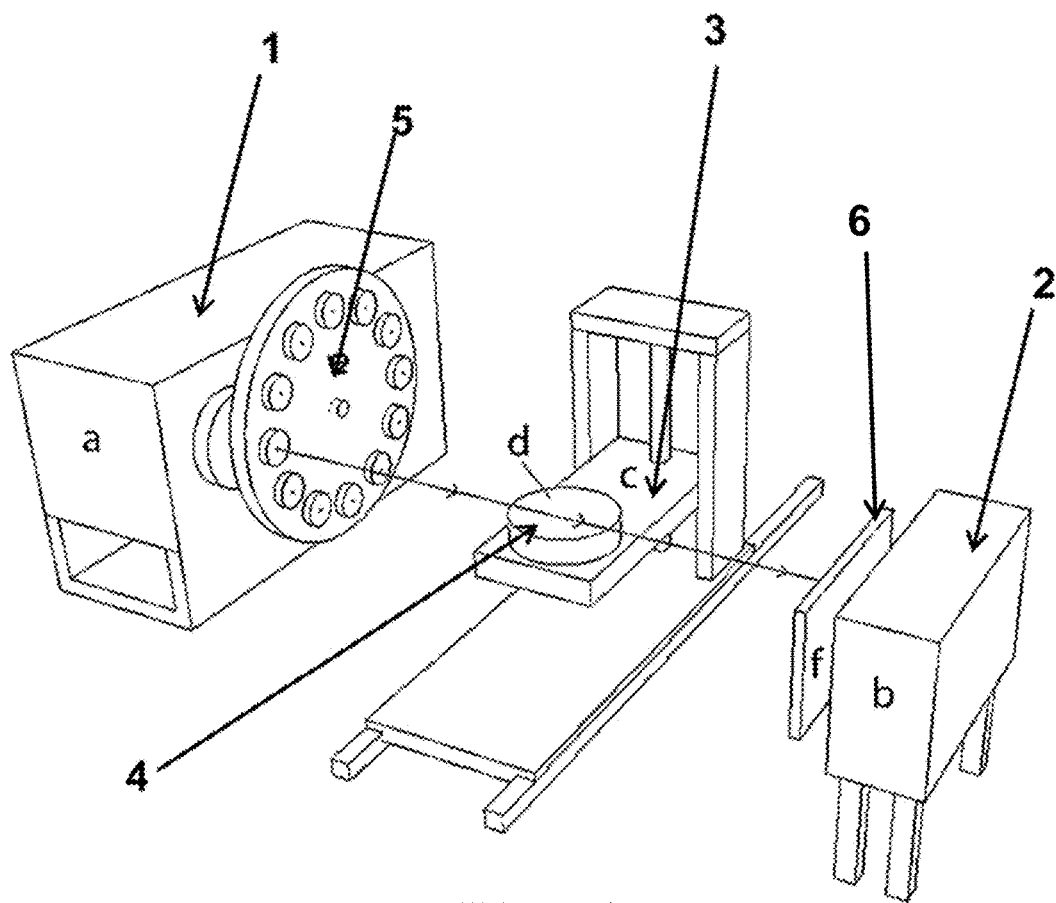
FIG. 1 illustrates a perspective drawing of a CT scanner according to the disclosure. The line with arrowheads shows the path of the X-ray beam. The X-ray tube (1) emits X-rays that travel through a user-selected collimator on a Geneva wheel (5). The X-ray beam travels through the specimen under study, which is placed on a rotating stage (4) that rides on a vertical positioning stage (3). After passing through the specimen under study, the X-ray beam travels through a detector-side collimator (6) and impinges upon a photomultiplier detector (2)

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

DEFINITIONS

The term "computed tomography" as used herein refers to cross-sectional images of an object reconstructed by collecting and integrating a plurality of x-ray projection data from different projection angles. In a typical CT system, x-rays emitted from an x-ray source pass through a portion of the target object, and are detected by a detector array. The portion of the object is irradiated from many different directions, for example by rotating the x-ray source and a detector array around the object. In a spiral (or helical) CT system, the x-ray source together with the detector array rotates continuously as the object is moved through the x-ray scan field, so that a continuous set of projection data is obtained for the entire region scanned.

The detector array measures the intensity of the x-ray beam that has traversed a portion of the object being scanned, which in the disclosure is an onion other plant structure. The portion of the material that is irradiated by an x-ray beam attenuates the beam by absorbing and/or scattering the x-rays. The imaged quantity is thus the spatial distribution of the attenuation coefficient inside a region of interest within the irradiated portion of the object. Various calibrations and corrections are performed to calibrate and correct the imaged quantity to approximate physical properties of the scanned materials, such as mass density and atomic number of the scanned materials. The detector array generates data indicative of the attenuated intensities of the x-rays that have traversed the material, digitizes them, and transmits the digitized detection signals to an image reconstruction system.

The image reconstruction system implements reconstruction algorithms and other image processing techniques, known in the art, to generate a CT image of the object, either slice by slice or volume by volume. In helical CT scanning, different reconstruction algorithms are known in the art such as Nutating Slice Reconstruction (the "NSR") algorithm (described in U.S. Pat. No. 5,802,134). Recent advances in the reconstruction algorithms allow improvement of image quality when a scanning geometry generates projection data that satisfy the completeness conditions for exact reconstruction as used in A. Katsevich. (2002) "Theoretically exact FBP-type inversion algorithm for spiral CT," *SIAM J. Appl. Math.*, 62: 2012-2026 and Kudo et al., (2000) "Quasi-exact filtered backprojection algorithm for long-object problem in helical cone-beam tomography," *IEEE TRANSACTIONS ON MEDICAL IMAGING*, 19: 902-921. These references are incorporated herein by reference in their entirety.

Conventional x-ray sources may include, for example, a thermionic x-ray tube, which produce x-rays by accelerating electrons through an electric field. A conventional thermionic x-ray tube typically includes an electron source (or cathode) for generating electrons, and an x-ray target (or anode) containing x-ray emissive material adapted to emit x-rays in response to incident electrons that have been accelerated by an accelerating electric field. The electric field may be established by means of a voltage provided to the x-ray ray source by a high voltage power supply. X-rays are generated due to the interaction of the accelerated electrons with the electrons and the nuclei that make up the atoms of the target material. The generated x-rays radiate from a spot on the x-ray target (or anode), commonly called the focal spot.

The term "onion (*Allium cepa*)" as used herein refers to the bulb onion or common onion, used as a vegetable and is the most widely cultivated species of the genus *Allium*. This genus also contains several other species variously referred to as onions and cultivated for food, such as the Japanese bunching onion (*A. fistulosum*), the Egyptian onion (*A. proliferum*), and the Canada onion (*A. canadense*). *A. cepa* is exclusively known from cultivation and its ancestral wild original form is not known, although escapes from cultivation have become established in some regions. The onion is most frequently a biennial or a perennial plant, but is usually treated as an annual and harvested in its first growing season.

The onion plant has a fan of hollow, bluish-green leaves and the bulb at the base of the plant begins to swell when a certain day-length is reached. In the autumn the foliage dies down and the outer layers of the bulb become dry and brittle. The crop is harvested and dried and the onions are ready for use or storage. The crop is prone to attack by a number of pests and diseases, particularly the onion fly, the onion eelworm and various fungi that cause rotting. Some varieties of *A. cepa* such as shallots and potato onions produce multiple bulbs. Most onion cultivars are about 89% water, 4% sugar, 1% protein, 2% fiber and 0.1% fat. Onions contain low amounts of essential nutrients, are low in fats.

Onions suffer from a number of plant disorders. The most serious for the home gardener are likely to be the onion fly, stem and bulb eelworm, white rot and neck rot. Diseases affecting the foliage include rust and smut, downy mildew and white tip disease. The bulbs may be affected by splitting, white rot and neck rot. Shanking is a condition in which the central leaves turn yellow and the inner part of the bulb collapses into an unpleasant-smelling slime. Most of these disorders are best treated by removing and burning affected plants. The larvae of the onion leaf miner or leek moth (*Acrolepiopsis assectella*) sometimes attack the foliage and may burrow down into the bulb.

Neck rot is a fungal disease affecting onions in storage. It is caused by *Botrytis allii* that attacks the neck and upper parts of the bulb, causing a grey mold to develop. The symptoms often first occur where the bulb has been damaged and spread downwards in the affected scales. Large quantities of spores are produced and crust-like sclerotia may also develop. In time a dry rot sets in and the bulb becomes a dry, mummified structure. This disease may be present throughout the growing period but only manifests itself when the bulb is in store. Anti-fungal seed dressings are available and the disease can be minimized by preventing physical damage to the bulbs at harvesting, careful drying and curing of the mature onions and correct storage in a cool, dry place with plenty of circulating air.

It is contemplated, however, that the methods of the disclosure are suitable to be applied to any plant bulb including the onion, shallot, garlic, leek and the like that may be susceptible to a disease that results in voids (gaseous or liquid) forming between leaf layers of the bulb.

Description

*Botrytis* Rots:

Bulb rot caused by species of fungus of the *Botrytis* genus is recognized as one of the most common and devastating onion storage diseases. There are seven named species of *Botrytis* that are associated with onion disease, and of these, five are recognized as causal agents of neck rot in onion bulbs. The species *B. aclada*, *B. allii*, and *B. byssoidea* are most commonly associated with fungal neck rots of onions in storage. *Botrytis* infections typically begin as a watery decay at the top of the bulb where the leaves have been removed. This decay progresses to the interior of the onion, causing the bulb to eventually rot from the inside out. Human visual inspection, the method most onion packing houses employ to discard damaged or diseased onions, is notably incapable of detecting internal *Botrytis* infections.

There are several ways *Botrytis* fungi can infect onion bulbs. The fungi have been known to survive inside onion seed, causing neck rots once the plant is mature, they form sclerotia on decaying onion bulbs and foliage in the field that can opportunistically infect injured bulbs, and they form conidia that can be carried in the wind or lay dormant in the field before infecting the foliage of the plant and spreading to the bulb.

Environmental factors play an important role in determining disease incidence. Prolonged wet periods prior to harvest lead to increased incidence of neck rot, as do over-application of nitrogen fertilizer and overcrowding of plants in the field. Additionally, conidia formed under particularly cold conditions, have been found to lead to faster growing infections in onion tissues than those formed at higher temperatures. Because unpredictable climate patterns lead to increased or decreased incidence of *Botrytis* outbreaks from year to year, onion growers can face great difficulty in managing and predicting their crop yields.

*Burkholderia cepacia*:

Onion sour skin, caused by the bacterium *Burkholderia cepacia*, is a common and highly destructive onion disease, causing as much as 50% harvest losses during severe outbreaks. Though *B. cepacia* infections frequently present as a soft, slimy decay of the outer layers of the onion bulb that is readily identifiable to visual inspection, internal infection is also common and infected onions can pass inspection and be placed in storage where they can spread the infection to surrounding bulbs. Infection typically occurs when bacteria enter a wound, either on the surface of the onion bulb, or through the neck of the onion when the leaves deteriorate at plant maturity or through vulnerable new shoots as they emerge from the bulb.

*Burkholderia cepacia* is not a single species, but a complex of seventeen closely-related species of bacteria that occupy several ecological niches and are also known to cause infections in people with cystic fibrosis or compromised immune systems. *B. cepacia* species have been found as mutualistic symbionts in grasses and cereal grains. Because of the ubiquity of *B. cepacia* bacteria in nature, onion growers have experienced great difficulty in preventing infection of onion bulbs, and no known chemical controls exist.

Like *Botrytis* infections, *B. cepacia* infections are more prevalent when onion fields are particularly wet prior to harvest. Application of nitrogen-rich fertilizer late in the growing season coincides with higher incidence of *Burkholderia* infection. *B. cepacia* thrives at high temperatures, 30-35° C., and disease outbreaks are more common under hot, moist conditions at harvest time. Though onion growers can take some steps to mitigate the outbreak of sour skin such as carefully timing and dosing fertilizer applications, uncontrollable weather patterns have a greater effect on the prevalence of sour skin in a particular harvest, and better methods to detect latent infections are necessary to prevent the spread of the infection.

*Pseudomonas viridiflava*:

*Pseudomonas viridiflava* typically infects onion plants through their foliage, forming dark, wet oval-shaped lesions that appear along the leaves. Though most affected plants rot while still in the field, during excessively rainy or humid field conditions the bacteria can spread to the interior of the onion bulb, leading to postharvest infections in storage. Onion bulb scales affected by *P. viridiflava* are characterized by reddish discolored lesions that, while softer than healthy tissue, are firmer than those damaged by *B. cepacia*. The infection does not appear to spread readily throughout the onion bulb, but remains confined to individual scales, leading to a ring-shaped region of infection when the bulb is sliced into transverse cross sections.

Bulbs containing internal *P. viridiflava* infections may present a hazard to surrounding bulbs in storage, particularly if they are improperly or incompletely cured. The damaged tissues also tend to host secondary opportunistic pathogens that can spread to surrounding onions as the bulb decays. While *P. viridiflava* is not known to survive for long periods in soil or water, it does appear to survive as an epiphytic organism in association with several common species of weeds native to the Vidalia region of Georgia, making control of the bacterium difficult.

Mechanical Damage:

A common form of damage to onion bulbs is bruising due to rough handling during harvest or packing or being crushed under the weight of other onions. Bruise damage can result in internal separation of the layers of an onion bulb that may be difficult to detect externally. This bruising can disrupt cell walls, leading to the leakage of cellular contents between the onion scales, and providing a water and nutrient rich environment for pathogens.

Multi-Center Bulbs and Seed Stems:

Multi-center bulbs, or "doubles", result when a single onion plant produces more than one bulb, resulting in multiple growing centers sharing a common root base. Such multi-center bulbs can arise from a number of causes including plant density in the field and the age of seedlings at transplant as well as high nitrogen fertilization levels and water stress during early growth stages.

Multi-center bulbs are undesirable to commercial buyers, especially onion ring producers, who typically require that their bulk purchases consist of more than 70% single-center bulbs. The scales between the two growing regions inside a multi-center bulb also appear to provide favorable environments for the growth of sour skin infections, making them potential vectors for the spread of the bacterium to other onions in storage.

Seed stems and internal sprouts are also unfavorable onion characteristics, leading to hard, bitter-tasting leaves at the center of the bulb. Several factors affect the formation of seed stems in storage, including temperature, variation between different cultivars, and low nitrogen levels in the field. Properly curing the outer scales of the onion bulbs can help reduce the rate at which seed stems form as premature formation of these seed stems often occurs in response to stress caused by damage to the outer layers of the bulb. Damaged bulbs are more likely to harbor pathogens, thus the detection and removal of these damaged onions from storage can help prevent the spread of disease.

Sweet Onion Quality Control:

Diseased and damaged onions take up valuable space in controlled atmosphere storage that could be dedicated to healthy onions. Bruised, crushed, or damaged onions that enter controlled atmosphere storage tend to be more susceptible to post-harvest disease, and the addition of such onions to storehouses can lead to the spread of infections and substantial financial losses for onion producers. Thus, improved quality assurance technologies would lead to a grading system that would advantageously rate individual onion bulbs in terms of their storability, allowing onion producers to discard bulbs with latent infections and divert lightly damaged but still salable bulbs to immediate sale at fresh markets or for processed foods, while ensuring that only the most sound bulbs enter controlled atmosphere storage.

Methods of non-destructive onion postharvest disease detection can be divided into three classes: chemical detection, via gas chromatography or electronic nose technologies, of volatile metabolites associated with pathogen infection in onion bulbs; imaging technologies that detect damage or signs of infection on the surfaces or first inner scales of onion bulbs; and X-ray imaging modalities that detect internal damage and defects in onion bulbs.

Detection of volatile metabolites associated with onion pathogens using gas chromatography mass spectroscopy identified about 12 distinct volatile compounds associated with several pathogen species such as *Botrytis allii* that they injected into onion bulbs. Of these 12 compounds, 6 were only detected in pathogen-inoculated bulbs, and not in water-inoculated controls. Such results show promise in the development of a metabolic chemical fingerprint that could potentially be used in the detection of pathogen growth in storage facilities.

Hyperspectral imaging has been widely used in the agricultural field, owing to its ability to non-destructively detect differences in chemical compositions within a commodity. Wang (2012) developed such a system to discriminate healthy onion bulbs from those that had been inoculated with *B. cepacia*. It was found that near-infrared images of 1070 nm and 1400 nm combined with a support vector machine model could be used to successfully detect this bacterium with a classification accuracy greater than 87%, and data could be obtained from as deep as the third inner scale of the bulb. Such techniques can be useful in detecting and screening out onion bulbs that show the presence of *B. cepacia* but do not yet exhibit human-detectable signs of damage.

While Meglinski (2010) proposed an optical coherence tomography-based screening method to detect disease and bruise damage in intact onion bulbs. One drawback, however, is that it is only capable of imaging the outer layers of onion bulbs, limiting such methods to the detection only of surface defects.

Planar X-Ray Imaging:

Planar X-ray line scanning has been explored in recent years as a means to detect internal infections of onion bulbs. X-ray scanners have the ability to detect morphological features such as double onion bulbs that are less desirable to consumers, as well as the presence of foreign inclusions and seed stems. Bayesian and neural network-based classification systems have been developed that can automatically detect image features that indicative of disease. These systems were found to be about 90% effective. In field trials, a commercial X-ray line scanner system reliably detected signs of gross damage, but had accuracy scores under 90% and a false-positive rate exceeding 10% in detecting diseased or damaged onions. These accuracy and false positive rates, however, are not sufficient for use in actual onion packinghouse quality control.

Volumetric Imaging with CT and MRI:

CT imaging in quality control of agricultural commodities has been explored in only a very limited capacity. CT imaging of onion bulbs by Maw (1995) addressed the possibility of using CT to detect internal layer separation of bruise-damaged bulbs.

High resolution CT imaging has been used to determine water content and distribution in oak and spruce trees. By first imaging freshly harvested trunk and limb sections, then drying and re-imaging these same sections, it was possible to determine the localization and concentration of water inside the vascular tissues of the trees.

Donis-Gonzalez (2012) used response surface methodology plots for an automated image quality optimization system for quality assessment of chestnuts. Parameters such as tube voltage, current, and the thickness of CT slices were modified and a commercial scanner was used. The values of these parameters were plotted against image quality factors such as signal to noise ratio, volume accuracy, high contrast spatial resolution, and low contrast object detectability. By correlating high image quality scores with individual scan parameters, it was possible to mathematically determine optimal scan parameters. Individual scans were then visually inspected and rated by image analysis experts, and these ratings were compared to scores predicted by the statistical model. The statistical scores all fell within a 95% confidence interval of the human perceived quality scores.

Magnetic resonance imaging in concert with X-ray CT has been used to study the effects of pathogens on fruits. Both modalities have been used in an exploration of core breakdown in Conference pears, where both MRI and CT were effective for detecting core breakdown, though both modalities under-reported the actual size of the affected volume. MRI was slightly more reliable than CT in terms of volumetric estimation of browned tissues, as such tissues exhibited relatively uniform densities compared to healthy tissues. Different proton densities and mobility in these browned tissues were more easily detected by MRI. Also, by comparing NMR and CT images of decaying nectarines, it was possible to determine that woolly breakdown does not lead to pectin depolymerization, but to water redistribution and micro-scale gas pockets in the tissues of affected fruits. CT was more reliable diagnostic tool in this instance, owing to the reduction in tissue density caused by gas pockets.

Other research has focused on the use of CT in measuring progressive physical changes in fruits. CT imaging has been used to determine maturity levels of tomatoes. By examining X-ray attenuation values within seed-forming cavities in tomatoes, it was possible to assign green tomatoes to one of four separate maturity classes. Though average overall X-ray absorption values did not correlate to specific maturity classes, significant correlations were found between these maturity classes and the number of pixels in cross-sectional images exhibiting absorption values above a specific threshold.

CT imaging was also used to study physical changes in fruit maturity, specifically in peaches and mangoes. Moisture loss and increased pH was correlated with diminished X-ray absorption as peaches and mangoes ripened in storage after harvest. Linear regression models were generated that could be used to determine the age and quality of peach and mango tissue based on X-ray absorption as measured by a CT scanner.

The present disclosure encompasses embodiments of X-ray computed tomography-based methods for the detection of onion quality factors. Such methods are advantageous in detecting internal damage to onion bulbs due to bacterial and fungal rots and mechanical damage while also providing for the overall assessment of onion bulb quality and market value. Because CT images provide cross-sectional reconstructions of the subject under study, CT scans of onion bulbs can be used not only to detect damage from disease, but also cuts and bruises that increase an onion bulb's susceptibility to disease, and the presence of shoots or seed stems and overall shape of the bulbs.

Image Analysis by X-Rays and Computed Tomography:

In therapeutic and industrial X-ray equipment, X-rays are generated by accelerating electrons in an electric field which are directed to a metallic target. As these kinetic electrons impact the target, they decelerate and release energy in the form of high-energy photons. The maximum photon energy emitted is given by the relations to electron velocity, v, the mass of an electron, $m_e$, the fundamental charge of an electron, e, and the potential difference of the electric field used to accelerate the electrons, V:

$$E_{max} = \tfrac{1}{2} m_e v^2 = eV$$

Because the colliding electrons can interact with the metal target in a variety of ways and dissipate varying levels of energy, the X-rays emitted are not all at $E_{max}$, but exhibit a continuous spectrum of energies. Lower energy, or soft, X-rays are more easily absorbed by objects, whereas higher energy or hard X-rays are more readily transmitted through objects The transmission of a monochromatic X-ray beam through a solid object of homogeneous composition and density is expressed by Lambert-Beer's law:

$$N(x) = N_0 e^{-\mu x}$$

where $N_0$ is the number of incident photons impinging upon the object, x is a linear distance through the object in centimeters, $N(x)$ is the number of photons that have been transmitted through the object at depth x, and $\mu$ is the X-ray attenuation constant of the object in inverse centimeters. $\mu$ is a function of both the density of the material of which the object is composed as well as the energy level of the incident X-rays.

The intensity of a polychromatic X-ray beam transmitted through an attenuating object can be calculated from equation lambert Beer:

$$N = N_0 \cdot \int_0^{E_{max}} S(E) \cdot \exp(-\int \mu(E,x) dx) dE$$

where $S(E)$ is a function describing the spectral intensity of the X-ray beam at energy E as well as the detector's sensitivity to the X-rays at energy E, and $\mu(E,x)$ is the object's X-ray absorption coefficient at energy E and depth x through the object.

Dual-energy CT is a method whereby absorption is measured simultaneously or successively at two energy levels. From the projection, two values are obtained for transmitted intensity, $N_H$ and $N_L$ for the high-energy spectrum $S_H(E)$ and the low-energy spectrum $S_L(E)$, respectively. Correspondingly, two absorbance values, $A_H$ and $A_L$ are obtained. Frequently, the imaged sample can be approximated by a two-compartment model. In the example of the onion, the two compartments (or constituents) would be water and plant tissue. Absorbance of water is referred to as $\mu_w$ and that of plant tissue as $\mu_T$. Lambert-Beer's law can be applied for each energy level, where $\mu_w$ and $\mu_T$ are representative values for the high- and low-energy spectra:

$$I_H = I_0 \exp(-\mu_{B,H} D_B - \mu_{S,H} D_S)$$

$$I_L = I_0 \exp(-\mu_{B,L} D_B - \mu_{S,L} D_S)$$

For the measured absorbance:

$$A_H = \mu_{B,H} D_B + \mu_{S,H} D_S$$

$$A_L = \mu_{B,L} D_B + \mu_{S,L} D_S$$

Here, the unknown variables are the distance of the x-ray traveled through water, $D_w$, and the distance traveled through plant tissue, $D_T$. The specific values for $\mu_w$ and $\mu_T$ can be determined beforehand, for example, by scanning dried onion tissue and a water sample. At this point, the above equation system provides two equations for two unknowns, namely, $D_w$ and $D_T$. This approach allows to obtain two images through tomographic reconstruction, most important an image for the water content.

Tomographic Reconstruction:

In computed tomography, a spatially resolved map of the X-ray absorption coefficients throughout a two dimensional slice of an object is constructed. Multiple slices can be obtained to build a three dimensional image of the X-ray absorption in the object. This spatially resolved X-ray absorption map is realized by obtaining multiple parallel beam linear X-ray projections through the same object from different angles and employing computer algorithms to reconstruct the data. Typical CT scans obtain 180 to 360 of these projections with one degree rotation or less between projections so as to cover 180° or 360° through the object. The resulting collection of projection data is a sinogram, as local highly absorptive regions in the object being scanned result in sinusoidal dark regions running the length of the sinogram.

There are a number of reconstruction techniques that can be used to obtain a spatially resolved X-ray absorptivity map from a sinogram including arithmetic reconstruction techniques that treat the data as a series of linearly dependent equations. Arithmetic reconstruction requires extensive processing power, and most algorithms will not converge to a stable final solution without some interpolation of missing data. Even with modern hardware acceleration techniques to increase the solution of arithmetic reconstructions to real-time speeds, the final image results are frequently no better than those obtained with less processor-intensive methods.

Another technique is to solve the reconstruction in the frequency domain. According to the Fourier Slice Theorem, a Fourier transform of a line from a sinogram obtained at rotation angle $\theta$ is the same as the Fourier transform of a slice through the object being scanned running through the origin and slicing through the object at angle θ These Fourier-transformed projections can be radially arranged at the center of a placeholder image, and an inverse Fourier transform of this place holder will reveal the cross section of the object being scanned. The main drawback of this technique is that the place holder image will contain large quantities low-frequency data toward the center of the image where the scan coverage is greater, but high frequency data at the far edges of the image are sparse unless many more time-consuming projections are obtained. The dearth of high frequency data leads to loss of image sharpness, particularly of the edges of features and fine textures. Fourier reconstruction of sinograms frequently relies on data interpolation to artificially recover these high frequency image components.

All reconstruction techniques described above, Fourier-domain reconstruction, ART, and filtered backprojection, allow the use of dual-energy projection information. For a dual-energy system, two spatially resolved maps can be obtained, the spatially resolved contribution of water to the absorption, and the contribution of plant tissue to the absorption. The water image provides pixel values that are proportional to the water content at that specific location. In a healthy onion, water is distributed very evenly inside the layers, but water content changes dramatically when bacterial or fungal rot is present. Therefore, the image analysis methods (segmentation and shape classification) are applicable to the water image as well and provide additional information for the classifier.

Most medical and industrial CT scanners rely on a technique known as filtered back projection to reconstruct sinograms. In filtered back projection, the lines from the sinogram are rotated by the angle at which they were obtained and "smeared" along the X-ray beam path into a new place holder image. These back projections sum to form a blurred reconstruction of the original image. This blurring is a side effect of the 1/r point spread that emerges due to the overlapping back projections. The projections can be filtered in the frequency domain prior to back projection to correct this blur, and several specialized filters have been developed that not only remove blur, but also remove image noise or enhance certain features.

All CT images obtained by the methods of the disclosure incorporate reconstructions using the filter kernel developed by Shepp and Logan (1974). The Shepp-Logan filter kernel attenuates the low frequency spectral components of an image to compensate for the 1/r point spread, while also slightly attenuating the highest frequency spectral components that are typically caused by noise. The Shepp-Logan filter, therefore, provides a compromise between image sharpness and noise attenuation.

Though reconstruction techniques convert sinogram images into planar mappings of X-ray absorption coefficients, they must be normalized if they are to be compared to other reconstructed images. Several factors affect the intensity of emitted and detected X-rays, and these high levels of variability can make comparisons between two images, even those obtained within the same CT scanner, difficult to compare reliably. Ambient temperature, power fluctuations, and age of the X-ray tube are just a few factors that can affect X-ray absorption values in images. To control for this variability, the absorption value of water in a particular CT scanner is obtained by scanning a phantom, the absorption values in the image are normalized according to this value, and this normalized value is multiplied by 1000:

$$I_{Houndsfield} = \frac{\mu_{pixel} - \mu_{water}}{\mu_{water}} \cdot 1000$$

Pixels in the image corresponding to water, therefore, have a value of 0, whereas low density materials have negative values (air has a Hounsfield value of −1000), and materials of higher density than water have Hounsfield values greater than 0.

Image Analysis (Cluster Analysis):

In reconstructed CT images, regions of an object with low X-ray absorptivity (i.e. low density) appear as dark pixels, whereas denser, more X-ray absorptive regions appear as brighter pixels. Using these properties, one can segment regions of an image into low density and high density components based on the pixel intensity values of the regions. One of the simplest methods of image segmentation is a bimodal operation in which a threshold value is selected, and pixels in the image with intensity values below this threshold are determined to be background and are separated from pixels whose intensity values are equal to or above this threshold value.

Groups of adjoining pixels that have been segmented from the image's background are known as clusters or features. There can be several distinct clusters within a single image. Since the size and shape of these clusters or features are determined by actual physical properties of the object being analyzed, analysis of these traits can yield information about the physical structures of the object under study. The size of a feature can be determined by counting the number of pixels within its borders. If the resolution of the image is calibrated to real world units, this pixel surface area can be correlated with the physical size of the associated structure in the object under study.

The aspect ratio of a cluster is a quantitative measure that describes the shape of the cluster in terms of its width and height. The centroid of the cluster is determined, and the maximum distance between the centroid and the boundary of the cluster, as well as the maximum distance between the centroid and boundary are calculated. The aspect ratio is the ratio of these two distances. Thus, a circle has an aspect ratio of 1, whereas elongated or elliptical shapes have aspect ratios greater than 1.

The compactness of a cluster is the squared length of its perimeter divided by its surface area. As the most compact shape possible is a circle (lowest ratio of perimeter to surface area), clusters exhibiting high compactness values may exhibit highly irregular outlines or may be greatly elongated. The discrete nature of image pixels can be a problem when computing these metrics, as the physical object being imaged may have regions that are so small that their boundaries cannot be accurately represented at the resolution that the scanner is capable of obtaining.

Irregularity is an additional measure that can indicate how irregular the outline of a cluster is. The irregularity is the ratio of the standard deviation to the mean value of the distance from the cluster's centroid to its outer perimeter. Clusters with irregular outlines have higher computed irregularity values, whereas elliptical shapes with smoother outlines have lower irregularity values. Therefore, this measure is a better indication of the characteristics of the outline of a cluster, whereas compactness simply indicates how circular a cluster is.

Fourier Shape Descriptors:

A cluster can be described in terms of the distance between its centroid and the points that make up its outer perimeter. This perimeter can effectively be "unrolled," and described as a function of distance from centroid versus angle. As the outer perimeter of a cluster is a closed shape, this function is periodic, and can be analyzed using the Fourier transform. A perfect circle has a constant distance between its centroid and outer perimeter; therefore its spectral decomposition will yield only a single frequency component in Fourier space. An ellipse will yield two frequency components correlating with its major and minor radii, and irregular shapes will have several frequency components. The equation showing the discrete Fourier coefficients $C_n$ are computed, where K is the period of the function and $r_k$ is the cluster's radius at angle k is:

$$C_n = \frac{1}{K}\sum_{k=0}^{K-1} r_k \cdot \exp\left(-\frac{2\pi jnk}{K}\right)$$

As $C_0$ is the mean radius of the cluster being studied, a size invariant form of the Fourier descriptors, $\zeta_n$, is used, which normalizes all coefficients by this mean radius:

$$\zeta_n = C_n/C_0$$

The value of Fourier shape descriptors is their ability to quantify abrupt changes in the outer perimeter of a cluster. A round shape with a sharp divot in its surface, for example, will exhibit high values for high order coefficients.

The methods of the disclosure incorporated the use of a low-cost novel X-ray computer tomography scanner system. Four CT-based onion quality assessment experiments were undertaken:

1. Initial exploratory scans of pathogen-inoculated onion bulbs and phantom objects to characterize the CT scanner and determine optimal scan parameters
2. Transverse and longitudinal cross sectional scans of onion bulbs that were hypodermically inoculated with pathogenic bacteria
3. 3-dimensional scans of bulbs whose neck regions were inoculated with pathogenic bacteria or fungi
4. Transverse and longitudinal scans of onions were subjected to impact damage Apparatus:

Onion bulbs were scanned in a computed tomography (CT) scanner apparatus as shown in FIG. 1. Referring now to FIG. 1, this apparatus comprises a dual energy pencil beam X-ray emitter (1) from a dual energy X-ray absorptiometry (DEXA) machine and producing X-rays at 140 kV and 70 kV peak energies. The X-ray detector (2) is a photomultiplier tube (PMT) having an anode voltage that can be adjusted by the user to a maximum of 1 kV. The PMT and its associated driver circuitry convert incident X-ray intensity to a proportional voltage.

The overall sensitivity of this apparatus was adjusted through the anode voltage, and through gain-adjustable amplifiers that adjusted the overall signal levels before they are digitized and sent to a computer system for analysis. This amplifier system has an added capability of separate gain levels for the low energy 70 kVp X-rays and higher energy 140 kVp X-rays, allowing the user to increase the gain for the weaker 70 kVp signals and decrease the gain associated with the 140 kVp X-rays, preventing signal clipping.

Specimens are rotated and translated in the x and y dimensions between the X-ray emitter and detector by a mechanical positioning system (3) and rotational stage (4). The X-ray beam is collimated with two sets of apertures. A rotating wheel with 13 user selectable positions is placed directly in front of the X-ray emitter (5). In one embodiment of the apparatus, this wheel contained 0.6 mm, 2.25 mm, and 3.1 mm diameter round apertures as well as several slit apertures and a mirror for reflecting a laser beam along the approximate path of the X-ray beam so users can position the specimen being scanned more accurately. A second set of apertures is located on a brass plate (6) that is placed between the photomultiplier tube and the X-ray source. In some embodiments, this plate contained 0.6 mm, 1.0 mm, and 2.5 mm diameter round apertures for detector side collimation, and the user can position this plate so a desired aperture is directly in the path of the X-ray beam.

The apparatus is controlled by software allowing the user to specify the image acquisition mode, collimator settings, number of projections to obtain, angle between projections, and photomultiplier anode voltage. Acquisition modes include a 1-dimensional profile scan that moves the object under study laterally through the X-ray beam and produces a plot of the detected X-ray intensity versus lateral position. Such scans are useful to quickly verify that proper scan width and photomultiplier settings have been set. The scout scan mode combines multiple profile scans at varying y-positions to generate a two dimensional projection of the object, and is similar to a planar X-ray projection scan obtained line by line.

Figure 33:
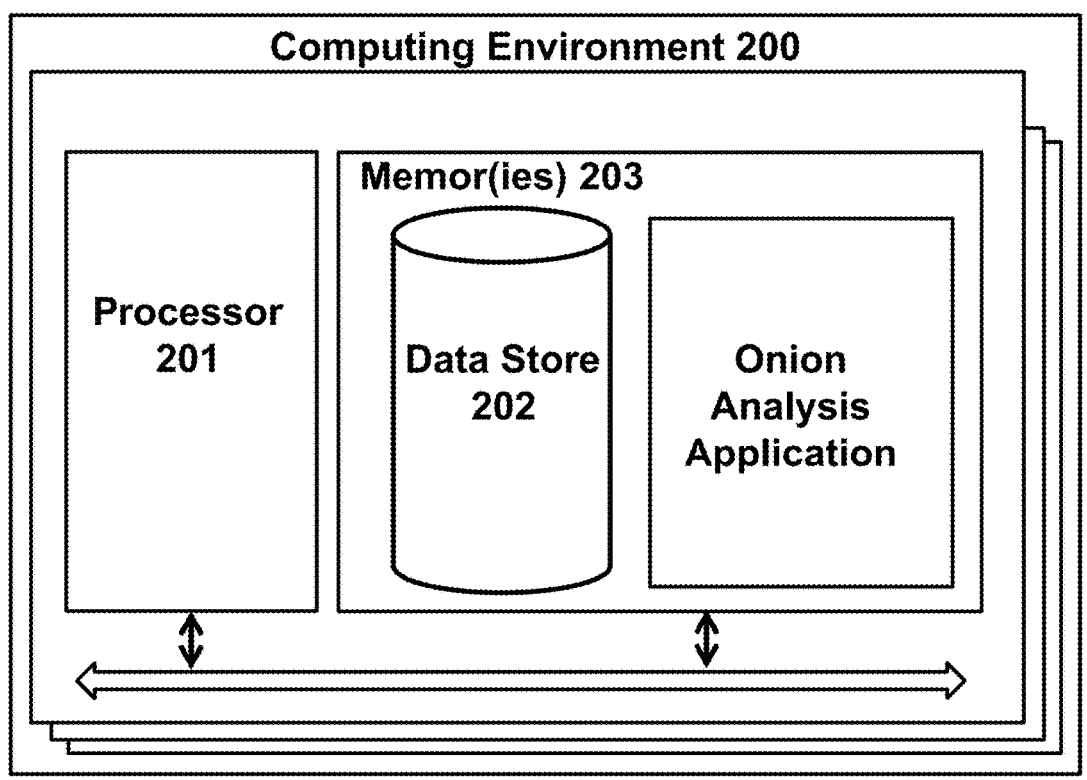
FIG. 33 schematically shows a computing system according to the disclosure.

Referring now to FIG. 33, various applications and/or other functionality may be executed in the computing environment 200 according to various embodiments. Also, various data is stored in a data store 202 that is accessible to the computing environment 200. The data store 202 may be representative of a plurality of data store 202s as can be appreciated. The data stored in the data store 202, for example, is associated with the operation of the various applications and/or functional entities described below.

The components executed on the computing environment 200, for example, may include a list of applications, and other applications, services, processes, systems, engines, or functionality not discussed in detail herein.

The client is representative of a plurality of client devices 204 that may be coupled to the network. The client may comprise, for example, a processor 201-based system such as a computer system. Such a computer system may be embodied in the form of a desktop computer, a laptop computer, personal digital assistants, cellular telephones, smartphones, set-top boxes, music players, web pads, tablet computer systems, game consoles, electronic book readers, or other devices 204 with like capability. The client may include a display. The display may comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The client may be configured to execute various applications such as a client application and/or other applications. The client application may be executed in a client, for example, to access network content served up by the computing environment 200 and/or other servers, thereby rendering a user interface on the display. To this end, the client application may comprise, for example, a browser, a dedicated application, etc., and the user interface may comprise a network page, an application screen, etc. The client may be configured to execute applications beyond the client application such as, for example, email applications, social networking applications, word processor, spreadsheets, and/or other applications.

A computing environment 200 according to an embodiment of the present disclosure may include one or more computing devices 204. Each computing device 204 may include at least one processor circuit, for example, having a processor 201 and a memory 203, both of which are coupled to a local interface. To this end, each computing device 204 may comprise, for example, at least one server computer or like device. The local interface may comprise, for example, a data bus with an accompanying address/control bus or other bus structure as can be appreciated.

Stored in the memory 203 are both data and several components that are executable by the processor 201. In particular, stored in the memory 203 and executable by the processor 201 are the main onion analysis applications, and potentially other applications. Also stored in the memory 203 may be a data store 202. In addition, an operating system may be stored in the memory 203 and executable by the processor 201.

It is understood that there may be other applications that are stored in the memory 203 and are executable by the processor 201 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 203 and are executable by the processor 201. In this respect, the term "executable" means a program file that is in a form that can ultimately be run by the processor 201. Examples of executable programs may be, for example, a compiled program that can be translated into machine code in a format that can be loaded into a random access portion of the memory 203 and run by the processor 201, source code that may be expressed in proper format such as object code that is capable of being loaded into a random access portion of the memory 203 and executed by the processor 201, or source code that may be interpreted by another executable program to generate instructions in a random access portion of the memory 203 to be executed by the processor 201, etc. An executable program may be stored in any portion or component of the memory 203 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 203 is defined herein as including both volatile and nonvolatile memory and data storage components. Volatile components are those that do not retain data values upon loss of power. Nonvolatile components are those that retain data upon a loss of power. Thus, the memory 203 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device 203.

Also, the processor 201 may represent multiple processors 201 and/or multiple processor 201 cores and the memory 203 may represent multiple memories 203 that operate in parallel processing circuits, respectively. In such a case, the local interface may be an appropriate network that facilitates communication between any two of the multiple processor 201s, between any processor 201 and any of the memories 203, or between any two of the memories 203, etc. The local interface may comprise additional systems designed to coordinate this communication, including, for example, performing load balancing. The processor 201 may be of electrical or of some other available construction.

Although applications, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

A module, segment, or portion of code that comprises program instructions to implement the specified logical function(s) may be embodied in the form of source code that comprises human-readable statements written in a programming language or machine code that comprises numerical instructions recognizable by a suitable execution system such as a processor 201 in a computer system or other system. The machine code may be converted from the source code, etc. If embodied in hardware, each block may represent a circuit or a number of interconnected circuits to implement the specified logical function(s).

Although the disclosure provides embodiments of a specific order of execution, it is understood that the order of execution may differ from that which is depicted. For example, the order of execution may be scrambled relative to the order shown. Also, blocks in succession may be executed concurrently or with partial concurrence. Further, in some embodiments, one or more of the blocks may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processor 201 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device 203.

Further, any logic or application described herein may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device, or in multiple computing devices in the same computing environment 200. Additionally, it is understood that terms such as "application," "service," "system," "engine," "module," and so on may be interchangeable and are not intended to be limiting.

The low-cost CT scanner apparatus used in this project proved to be a reliable instrument for the imaging of agricultural specimens for quality control purposes. Mechanical stability was found to be of paramount importance, as even small vibrations or shifts of the object under study caused ghosting and blurring in reconstructed images. Collimation of the X-ray beam also proved to be an important factor affecting image contrast and sharpness. A round aperture with a 0.6 mm diameter at the X-ray beam and a 2.5 mm diameter aperture at the X-ray detector offered the best compromise between contrast and sharpness. Finally, the anode voltage of the photomultiplier X-ray detector was adjusted to provide a wide range of pixel intensity values without saturating the detector. A setting of 800 V was found to be ideal for this particular apparatus.

*B. cepacia* was found to grow readily in laboratory-inoculated Vidalia sweet onions, and lesions on onion bulb tissues were evident within 10-21 days after inoculation. Once damage was evident, the onion bulbs decayed rapidly over the course of 2-3 days. Surface damage to the onions caused irregularities in the bulbs' outlines in several cases, and these surface irregularities were detectable with binary image thresholding and Fourier shape analysis. Internal damage was characterized by crescent-shaped regions of low density in the interior of the bulb in transverse cross section exhibiting large compactness values. Additionally, smaller dark regions tended to cluster around the point of infection near the periphery of the bulb, providing another possible cue for detection of this pathogen in harvested onions.

*P. viridiflava* did not grow as readily or as fast as *B. cepacia* and only two of the four specimens exhibited any signs of infection by the end of the experiment. In both of the specimens that exhibited damage, transverse cross sectional images revealed small, round lesions near the outer edges of the bulbs.

In several instances, longitudinal cross section images of the bulbs provided a clearer view of pathogen damage as well as the progress of pathogens inside onion tissues. However, natural morphological variation between individual onion bulbs can make automated segmentation and characterization of damages difficult in images obtained at this projection orientation. Furthermore, each onion being imaged would have to be rotated about its root-shoot axis and reimaged repeatedly to obtain sufficient coverage to locate localized damages. Multiple transverse images, by contrast, can be more easily obtained via a multi-slice clinical CT scanner, and these slices have the advantage of more simplistic geometry (concentric circular rings), greatly simplifying the process of automatically and programmatically identifying damages or other undesirable features.

The crescent shaped dark regions associated with *B. cepacia* were also found in transverse images of the Vidalia onion bulbs whose necks were inoculated with *B. allii*. These damaged regions, upon segmentation and shape analysis, tended to exhibit large compactness values and low irregularity values, as these elongated shapes tended to remain constrained within specific layers in the onion bulbs. In some cases, longitudinal cross sections elucidated the path of the pathogen's damage throughout the onion bulb, but the high variability in onion tissue morphology in this projection made automated image processing extremely difficult.

The Peruvian-grown sweet onions did not decay as readily as the Vidalia-grown onions when inoculated with *B. allii, B. cepacia*, and *P. viridiflava*. However, these were found to be more likely to have multiple centers, and texture analysis was used to discriminate single center bulbs from those with multiple centers. By running a 3×3 pixel variance operator on multiple transverse cross sections obtained at differing depths over the onion, small dark voids that occur at the junctions of multiple centers were emphasized. These cross section images were then $\zeta$-projected to form a single transverse image. Onion bulbs with multiple centers exhibited multiple "hot spots", near the center of the bulbs, whereas single center bulbs did not.

Onions subjected to drop damage did not display signs of damage in CT images until a couple days after being damaged. Bulbs subjected to repeated low impact forces displayed internal signs of damage, as did those subjected to single high impact events, though none of these bulbs exhibited external signs of damage.

As bruise damage tends to be localized to a specific section of the bulb near the outer layers, methods were developed to pinpoint the point of impact and determine the likelihood that dark regions detected in transverse cross section images were due to bruise damage and not pathogen infection. The weighted damaged area function assigns weighting coefficients to segmented features based on their distance from the center of the onion bulb, and this metric was useful in eliminating features near the center of the bulb, leaving only those that were likely caused by mechanical impacts. Damage localization metrics also help to discriminate bruise damage from other types of damage or naturally occurring dark regions in transverse images by providing a center of impact and likelihood neighborhood surrounding this calculated impact center. Bulbs exhibiting large likelihood neighborhoods have more diffuse damage that is less likely due to impact forces, whereas small neighborhoods are indicative of the localized damage associated with impact damage.

One aspect, therefore, of the disclosure encompasses embodiments of a method of determining the quality of an onion bulb, said method comprising the steps of: (a) acquiring at least one CT image of an onion bulb; (b) adjusting the quality of the CT image to remove noise, enhance the contrast of the image and to enhance the edge of the image of the onion bulb; (c) identifying the outline of the onion bulb; (d) identifying the interior voids of the onion bulb; (e) obtaining a shape description of the onion bulb; (f) obtaining quantitative measurements of the interior voids of the onion bulb, wherein said measurements are of the relative sizes of the voids, the shapes of the voids, and the location of the voids relative to the internal layers of the onion bulb; and (g) classifying the onion bulb with respect to at least one of: the quality of the onion as a marketable product, a disease type generating the voids in the onion bulb, and the extent of the progress of the disease within the onion bulb.

Another aspect of the disclosure encompasses embodiments of a non-transitory computer-readable medium embodying a program executable in at least one computing device, comprising code that: accesses a computed tomography (CT) image of an onion bulb; identifies an outline of the onion bulb in the CT image; identifies a plurality of interior voids of the onion bulb; generates a shape description of the onion bulb based at least in part on the plurality of interior voids, the outline of the onion bulb, or a combination thereof; generates a plurality of measurements for the interior voids of the onion bulb; and generates a classification for the onion bulb describing a condition of the onion bulb based at least in part on the plurality of measurements, the shape description, or a combination thereof.

In some embodiments of this aspect of the disclosure, the plurality of measurements can comprise a relative size of at least one of the plurality of interior voids, a shape of the at least one of the plurality of interior voids, or a location of the plurality of interior voids relative to a plurality of internal layers of the onion bulb.

In some embodiments of this aspect of the disclosure, the condition of the onion bulb can further comprise a suitability of the onion as a food product, whether a disease exists the interior voids in the onion bulb, or an extent of a progress of the disease within the onion bulb.

In some embodiments of this aspect of the disclosure, the program can further comprise code that performs image processing of the CT image to adjust a quality of the CT image.

In some embodiments of this aspect of the disclosure, the program can further comprise code that generates a two-dimensional cross-sectional image describing a plurality of X-ray absorption values of the onion bulb.

In some embodiments of this aspect of the disclosure, the performing image processing can further comprise at least one of: removing noise from the CT image, enhancing a contrast of the CT image, or enhancing an edge of the CT image.

In some embodiments of this aspect of the disclosure, the performing image processing can further comprise generating a modified image of the onion bulb comprising only the plurality of interior voids of the onion bulb, wherein the classification is generated based at least in part on the modified image.

Yet another aspect of the disclosure encompasses embodiments of a system comprising: at least one computing device; and an onion classification application executed in the at least one computing device, the onion classification application comprising logic that: accesses a computed tomography (CT) image of an onion bulb; identifies an outline of the onion bulb in the CT image; identifies a plurality of interior voids of the onion bulb; generates a shape description of the onion bulb based at least in part on the plurality of interior voids, the outline of the onion bulb, or a combination thereof; generates a plurality of measurements for the interior voids of the onion bulb; and generates a classification for the onion bulb describing a condition of the onion bulb based at least in part on the plurality of measurements, the shape description, or a combination thereof.

In some embodiments of this aspect of the disclosure, the plurality of measurements can comprise a relative size of at least one of the plurality of interior voids, a shape of the at least one of the plurality of interior voids, or a location of the plurality of interior voids relative to a plurality of internal layers of the onion bulb.

In some embodiments of this aspect of the disclosure, the condition of the onion bulb can further comprise a suitability of the onion as a food product, whether a disease exists the interior voids in the onion bulb, or an extent of a progress of the disease within the onion bulb.

In some embodiments of this aspect of the disclosure, the onion classification application can further comprise logic that performs image processing of the CT image to adjust a quality of the CT image.

In some embodiments of this aspect of the disclosure, the onion classification application can further comprise logic that generates a two-dimensional cross-sectional image describing a plurality of X-ray absorption values of the onion bulb.

In some embodiments of this aspect of the disclosure, the performing image processing can further comprise at least one of: removing noise from the CT image, enhancing a contrast of the CT image, or enhancing an edge of the CT image.

In some embodiments of this aspect of the disclosure, the performing image processing can further comprise generating a modified image of the onion bulb comprising only the plurality of interior voids of the onion bulb, wherein the classification is generated based at least in part on the modified image.

Yet another aspect of the disclosure encompasses embodiments of a computer-implemented method, comprising: accessing, by at least one computing device comprising at least one hardware processor, a computed tomography (CT) image of an onion bulb; identifying, by the at least one computing device, an outline of the onion bulb in the CT image; identifying, by the at least one computing device, a plurality of interior voids of the onion bulb; generating, by the at least one computing device, a shape description of the onion bulb based at least in part on the plurality of interior voids, the outline of the onion bulb, or a combination thereof; generating, by the at least one computing device, a plurality of measurements for the interior voids of the onion bulb; and generating, by the at least one computing device, a classification for the onion bulb describing a condition of the onion bulb based at least in part on the plurality of measurements, the shape description, or a combination thereof.

In some embodiments of this aspect of the disclosure, the plurality of measurements can comprise a relative size of at least one of the plurality of interior voids, a shape of the at least one of the plurality of interior voids, or a location of the plurality of interior voids relative to a plurality of internal layers of the onion bulb.

In some embodiments of this aspect of the disclosure, the condition of the onion bulb can further comprise a suitability of the onion as a food product, whether a disease exists the interior voids in the onion bulb, or an extent of a progress of the disease within the onion bulb.

In some embodiments of this aspect of the disclosure, the computer-implemented method can further comprise performing, by the at least one computing device, image processing of the CT image to adjust a quality of the CT image.

In some embodiments of this aspect of the disclosure, the computer-implemented method can further comprise generating, by the at least one computing device, a two-dimensional cross-sectional image describing a plurality of X-ray absorption values of the onion bulb.

In some embodiments of this aspect of the disclosure, the performing image processing can further comprise at least one of: removing, by the at least one computing device, noise from the CT image, enhancing, by the at least one computing device, a contrast of the CT image, or enhancing, by the at least one computing device, an edge of the CT image.

In some embodiments of this aspect of the disclosure, performing image processing can further comprise generating, by the at least one computing device, a modified image of the onion bulb comprising only the plurality of interior voids of the onion bulb, wherein the classification is generated based at least in part on the modified image.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Figure 2:
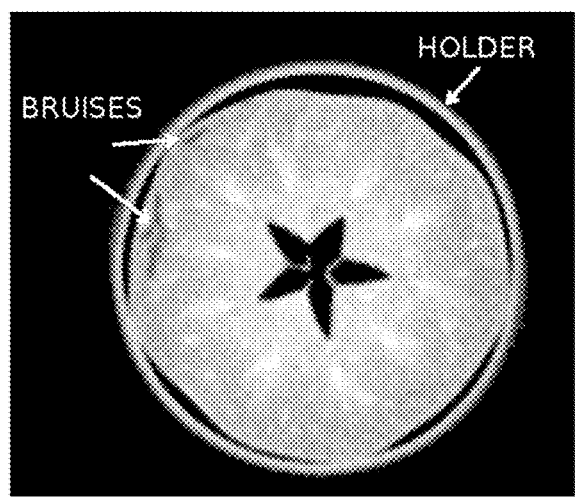
FIG. 2 is a digital image of a scan of an apple secured to the specimen stage in a plastic drinking cup. Darker shades indicate higher X-ray absorption.

FIG. 2 shows a scout scan of an apple. The cross sectional scan mode was prepared by scanning the object laterally, rotating it by a set amount, and repeating this lateral scan to produce a sinogram. By repeating this 2d scan at varying y-positions of the object and generating multiple sinograms, a 3-dimensional voxel reconstruction of the object was generated. In all scan modes, the high X-ray energy (140 kVp) and low X-ray energy (70 kVp) images were simultaneously acquired. The in-plane resolution of reconstructed cross sectional images was 0.5 mm$^2$, and a 3 dimensional mode with 0.5 mm slice thickness, isometric voxels was possible. As the diameter of the X-ray beam was effectively 0.6 mm with collimation, voxel dimensions less than 0.5 mm were impractical, though still technically possible.

Tomographic reconstruction was accomplished with the software package Crystal Image v.0.9.4, 0.9.5, and 0.9.6β. Raw sinograms were loaded into Crystal Image and the intensity of pixels associated with the (non-attenuated) X-ray beam through air was determined as a baseline value. The intensities of the pixels in the image were then scaled by this baseline value, and the logarithm of this ratio is the line integral of the absorption of the X-ray beam through the object. Finally, the Shepp-Logan back-projection reconstruction method was applied to this logarithmatized sinogram, yielding a two-dimensional cross-sectional image of the scanned object's X-ray absorption values. The reconstructed image was saved as a 32-bit floating point grayscale image in the TIFF image format for further analysis.

Example 2

Initial tests were conducted to ascertain the optimal operating parameters of the CT scanner. Such parameters include photomultiplier tube anode voltage settings, X-ray aperture sizes, and the number of projections necessary to build a sinogram that would yield sufficient image quality upon reconstruction to detect damage to the onion bulbs. Additionally, several methods of securing the onion bulbs in the path of the X-ray beam were tested, and the lateral movement stage inside the CT apparatus was modified to increase stability and dampen mechanical vibration.

Several Vidalia bulbs were inoculated with *B. allii, B. cepacia* or *P. viridiflava* as an initial test to determine whether damage caused by these pathogens was detectable with the CT apparatus. Overall sixteen total bulbs were scanned, four samples inoculated with each pathogen, and four untreated bulbs.

While more sinogram projections provide more information about the object being scanned, making for sharper and cleaner reconstructions, each scan obtained adds to the total time of image acquisition. A balance is necessary between scan time and image quality. Images were obtained with 360 sinogram projections (the object was rotated a full 360 degrees in one degree increments), 180 projections (180 degrees of rotation with 1 degree increments), and 90 projections (180 degrees of rotation with 2 degree angular increments). These sinograms were reconstructed, and the reconstructed cross sections were subjectively evaluated to determine which parameters provided the best balance of scan time and image quality.

The dynamic range of the image reconstructions is an important image quality factor. The optimal photomultplier anode voltage and X-ray aperture configurations were determined. Photomultplier anode voltage determines the sensitivity of the detector to the X-rays impinging upon it, and the X-ray apertures determine the overall density of the X-ray flux interacting with the detector. Setting a too low photomultplier anode voltage or too narrow aperture decreases the overall sensitivity of the system and results in images with a narrow range of pixel intensity values, making it difficult to differentiate between distinct regions inside the object being scanned. Setting the photomultplier anode voltage too high, or allowing too many X-rays the reach the detector by choosing a too large aperture results in clipping, that is, the actual X-ray intensity value is beyond the system's maximum detectable range, thus these high intensity values are clipped to this maximum value and data are lost.

To determine optimal detector anode voltages and apertures, a water phantom was scanned with the detector anode set to 600, 700, 800, 900, and 1000 volts, with beam aperture sizes of 0.6 mm and 2.25 mm, and a 2.5 mm detector side collimator. The phantom object was constructed out of a water-filled plastic drinking cup bolted to the rotational stage in the CT scanner. Because onion bulbs are composed primarily of water, this phantom object was considered a good approximation of an onion bulb. The reconstructed images were evaluated subjectively to determine the best combination of settings.

Finally, a two-channel switchable amplifier was added to the photomultiplier detector's output. This amplifier allows the user to specify separate gain levels for the detected signals resulting from 140 kVp and 70 kVp X-ray energies. Weak signals resulting from the 70 kVp X-ray beam could be greatly amplified at the expense of decreased signal to noise ratio, whereas the higher signal levels from the 140 kVp X-rays could be amplified less so as to avoid oversaturation and clipping.

Results (CT Scanner Mechanical Modification):

Initial tests of the CT scanner revealed image blurring that was thought to be due to mechanical vibration of the mechanical stages in the apparatus. As the x-dimension resolution of the scanner is 0.5 mm per pixel, even slight vibrations proved to result in unacceptable images.

Securing the Samples:

It is of importance to hold the onions securely and prevent them from moving during the scan, and alternative methods were, therefore, tested. A suitable adjustable onion holder was constructed out of polyacetal plastic, as shown in FIG. 3.

Figure 3:
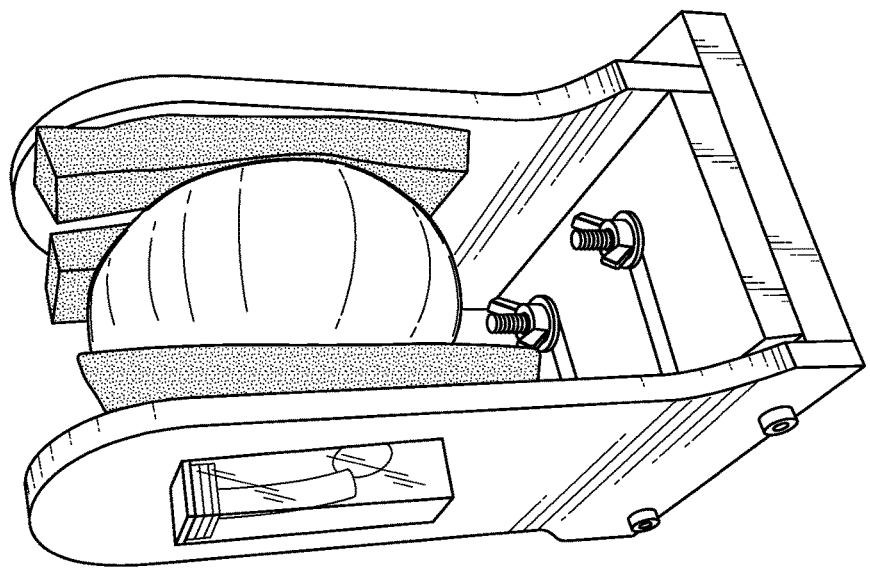
FIG. 3 illustrates an embodiment of an adjustable polyacetal onion holder with water phantom.
Figure 3:
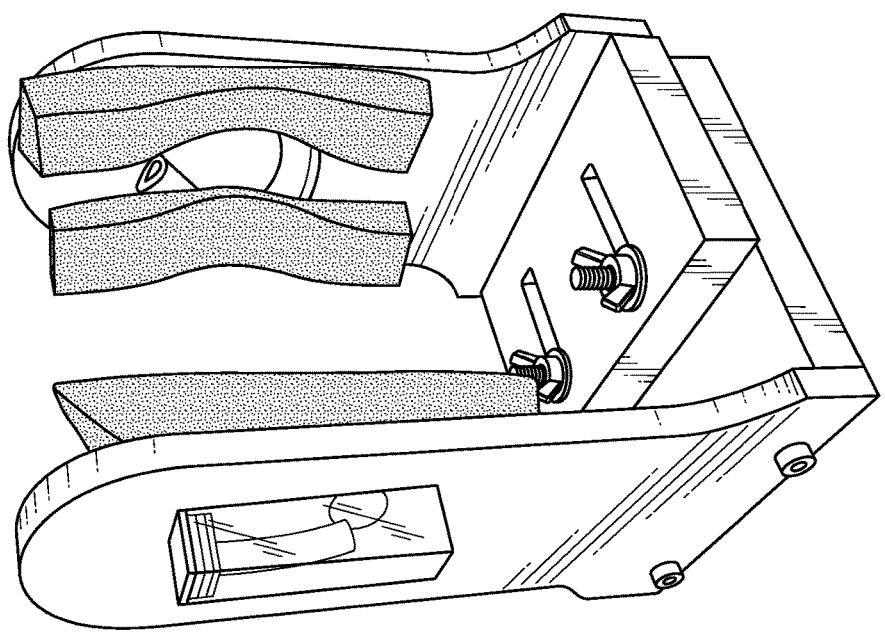

Referring now to FIG. 3, an L-shaped piece is bolted to the CT scanner's rotational stage, and another L-shaped piece is allowed to slide to accommodate larger or smaller onions. This movable section is secured to the other by way of machine screws and wing nuts. Large diameter holes have been drilled into the sides of the two L-shaped sections to allow onion roots or necks to protrude, making the holder ideal for securing onion bulbs for transverse cross section scans. This same holder was found to be useful for securing onions for transverse section scans as well, and was used exclusively for subsequent onion scans. Foam padding was added to the sides of the holder that contact the onion, as well as the edges of the bore holes to prevent damage to the onion bulbs. A plastic cuvette filled with water was secured to the outer edge of one of the sample holder sections, providing a water X-ray absorption reference.

Collimators and Photomultiplier Parameters:

Collimator pairings are important factors affecting image quality. Larger collimator apertures in front of the X-ray beam led to loss of fine detail in the reconstructed images, whereas small apertures in front of the PMT were found to attenuate the overall signal to the point that light-dark contrast was compromised. In every case, images obtained with the 1 mm collimator aperture in front of the PMT were found to have unacceptably low dynamic ranges and high noise content. Ultimately, it was determined that the 0.6 mm emitter aperture and 2.5 mm detector collimator provided an advantageous compromise between fine detail resolution and image contrast.

Figure 4A:
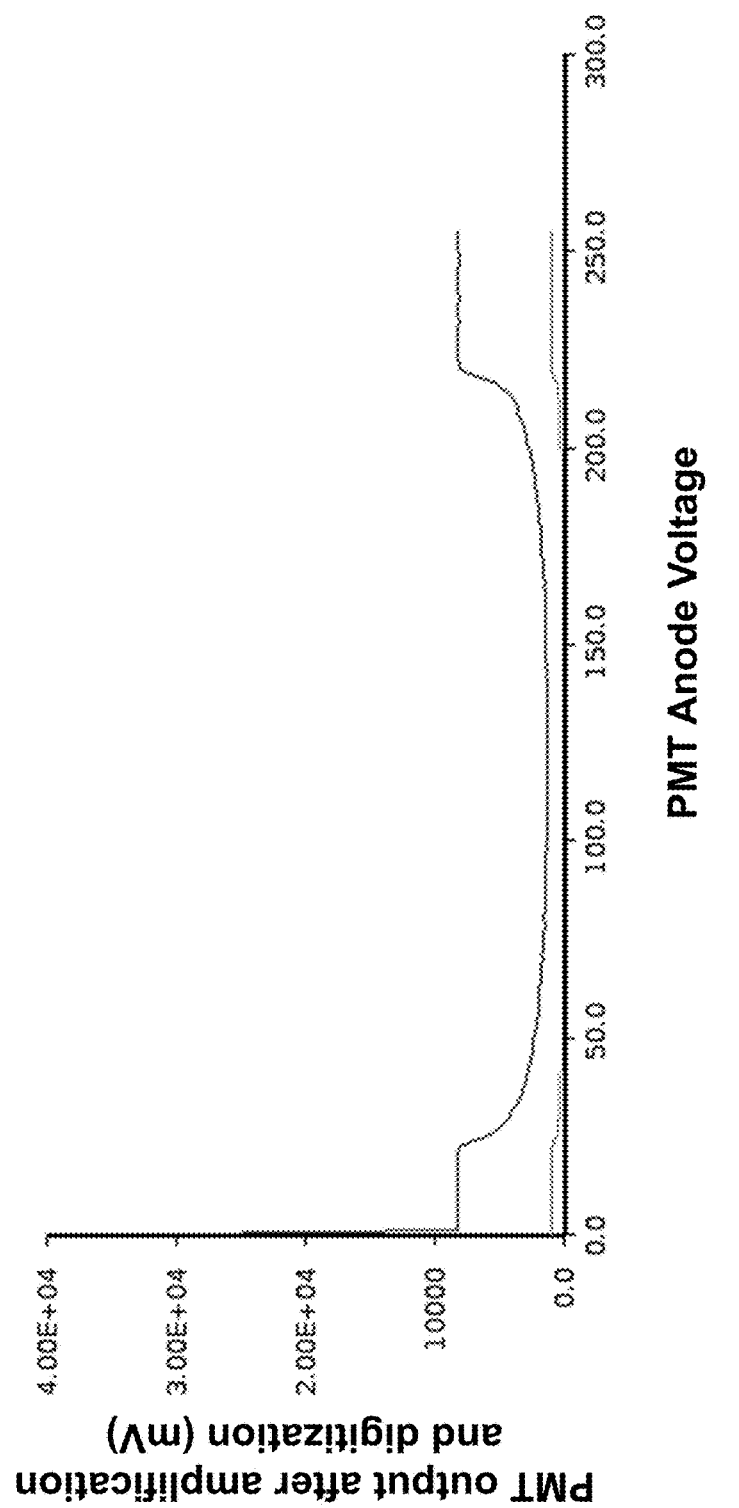
FIG. 4A is a graph illustrating the effect of adjusting the PMT anode voltage. The top line (140 kVp energy) shows a low range of values, likely due to clipping of the highest values. Y-axis values are the output from the PMT in mV that have been amplified and digitized. The bottom line illustrates the effects of setting the PMT anode voltage too low. Both the 140 kVp and 70 kVp plots show a low range of values. Reconstructions of such scans result in images with unacceptably high noise levels as well as poor contrast.

The photomultplier tube's anode voltage affects the image and its signal to noise ratio. Ideally, a line from a CT sinogram should exhibit a wide range of pixel intensities, with the highest intensities being associated with the unattenuated X-ray beam through air, and the lowest values associated with the attenuated X-ray beam through an absorptive object. High PMT anode voltages lead to increased sensitivity, but at the cost of dynamic range (FIG. 4A). There is also the potential that the highest recorded output values from the PMT are outside the operating range of the instrument's amplifiers, resulting in these values being clipped to the maximum possible output value of the circuitry. Low PMT anode voltages can lead to unacceptably low sensitivity, again reducing the dynamic range of the images, and decreasing the signal-to-noise ratio (FIG. 4A).

Figure 4B:
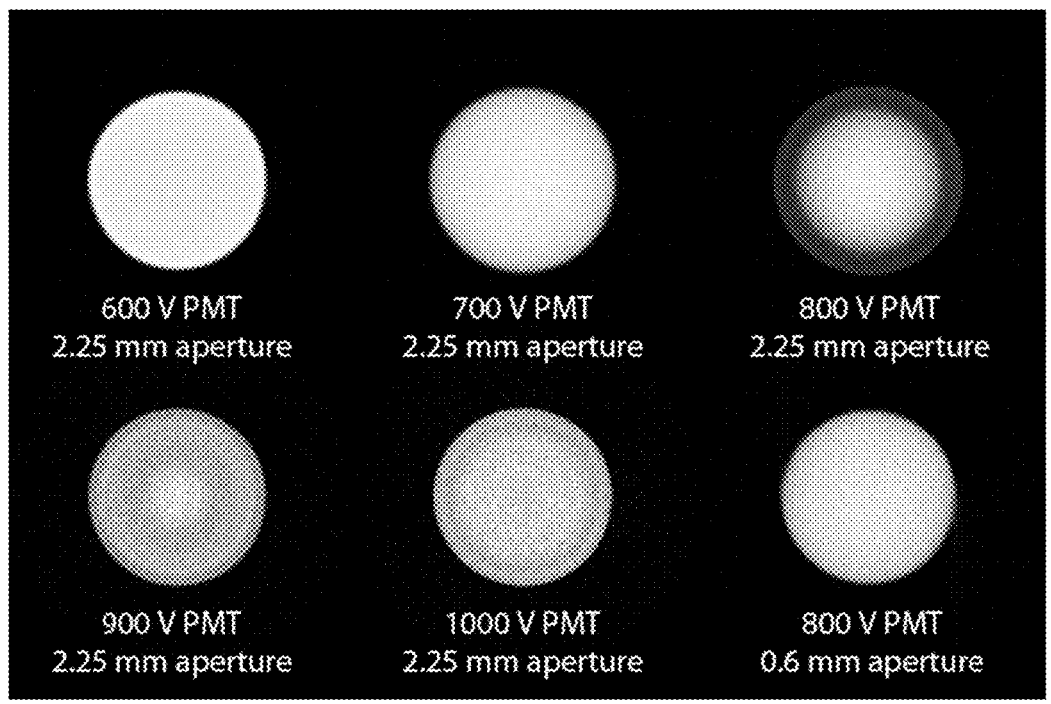
FIG. 4B illustrates water phantoms scanned under varying PMT anode voltages and beam aperture sizes with a constant detector collimator size of 2.5 mm. Images obtained with high PMT anode voltages and large apertures display the effects of detector clipping. The bottom right panel shows a scan of the phantom conducted under optimal settings: a 0.6 mm beam aperture, 2.5 mm detector collimator, and PMT anode voltage set to 800V.

A phantom was constructed out of a plastic drinking cup and filled with water. This water phantom was scanned under several combinations of PMT anode voltages and apertures. FIG. 4B shows the results of these scans. With the 2.25 mm X-ray beam aperture, the effects of clipping become apparent at PMT anode voltages of 800 and above. Subsequent scans of onion bulbs were obtained at a PMT anode voltage of 800V, with a beam aperture size of 0.6 mm and a PMT collimator size of 2.5 mm. Random sampling of nine points in images obtained of the empty drinking glass at 70 kVp and 140 kVp yielded mean absorption values of 0.266 $cm^{-1}$ and 0.208 $cm^{-1}$ respectively, meaning the absorption values of the plastic drinking cup are very close to those of water.

Number of Projections:

In all cases, it was determined that angle between projections taken when producing a 2d scan should be as small as possible. More projections provide more information for the reconstruction algorithm. The effects of noise also tend to average out with a large number of projections. Images with larger rotational angles and fewer projections have lower resolution and apparent radial blurring of fine features due to aliasing.

One final factor potentially affecting image quality is the alignment of the rotational stage with respect to the X-ray beam. When conducting a full 360 degree scan of an object, it was necessary that the rotational stage's axis of rotation be perpendicular to the x-direction translation stage's plane of travel. Non-perpendicular alignments lead to artifacts in reconstruction, as projections of the same location taken from diametric opposites of the object are not aligned. Such images are, however, recoverable, though the sinograms must be split into two 180° scans and reconstructed separately. The CT reconstructions from 180° sinograms were deemed to be of acceptable quality to locate damage in onion bulbs due to pathogen infection.

Example 3

Hypodermic Inoculation: The best two-dimensional projection images were determined for assessing damage caused by pathogens, and the progress of a pathogenic infection in the onion bulb was charted. Bacterial pathogens such as *B. cepacia* and *P. viridiflava* typically require a wound to enter onion bulb tissues, thus it was decided to use hypodermic needles to introduce the bacterial pathogen cultures to the sample onion bulbs.

Procedure and Imaging Protocol:

The onions were stripped of their dry outer skins and submerged in a 2% sodium hypochlorite solution for 1 min to sterilize the surface of the bulb. Prior to inoculation, the onions were pre-screened for signs of infection or damage via visual inspection, and imaged by CT in transverse and longitudinal projections to obtain baseline pre-infection images and to confirm that there were no internal defects.

Bacterial colonies were swabbed from culture plates and suspended in 5 mL sterilized water. Approximately 0.3-0.5 mL of the bacterial suspension was injected approximately 1-2 cm deep into the side of the bulb with a 19 gauge hypodermic needle, and the injection site was marked with a permanent marker. The inoculated onions were placed individually into plastic bags to prevent cross-contamination and to provide a high humidity environment for the pathogen to grow. Onions inoculated with *B. cepacia* were placed in an incubator set to 30° C., while onions inoculated with *P. viridiflava* were placed in the dark at room temperature.

The location of the cross-sectional scans was chosen so the scan plane coincided with the injection site of the hypodermically inoculated onion bulbs so that damage to the onion tissues caused by the bacteria would first be evident in the immediate vicinity of the injection site. The pathogen-inoculated onion bulbs were imaged at 3-7 day intervals over the course of a 28 day long incubation period in transverse and longitudinal cross sections until clear signs of damage were evident.

Image Analysis:

The 140 kVp X-ray energy level sinograms were reconstructed with Crystal Image v.0.9.5 and saved as 32-bit signed floating point TIFF files. After reconstruction, negative-valued pixel intensities existed throughout the image; such physically impossible values were a side effect of the filtered backprojection reconstruction technique used to reconstruct the images, and Crystal Image's soft thresholding algorithm was applied to the image to clip any negative values to zero.

The images were then converted to a 16-bit integer format that is more widely recognized by other image processing software packages via a custom program written in the C programming language. Images were imported into Adobe Photoshop CS4 (version 11.0), and an image gallery of each specimen was constructed so as to show the progression (or lack thereof) of the pathogen infections in the bulbs. To prevent the plastic specimen holders and foam cushioning from interfering with these additional image analysis procedures, they were manually painted out of the images with Photoshop.

For analysis of internal features, the unmodified transverse cross-section images were opened in Crystal Image, a 3×3 Gaussian blur was applied, and the bi-level binary threshold algorithm was applied such that internal voids and lesions in the images showed up as black features inside the white bulb silhouette. The black-white image values were then inverted so the image background appeared white in color, the bulb tissues appeared as black, and the voids and lesions inside the bulb appeared as white. The now white image background was flood filled with black, resulting in a final image consisting only of the isolated voids and lesions on a black background. Crystal Image's "Cluster Labeling" command was then applied to the image. This command computed the size, aspect ratio, compactness, and irregularity of each isolated onion damage feature, and these feature characteristics were saved in tabular format in a text file for further analysis.

For analysis of the outer edges of the onion bulbs, transverse cross section images were opened in Crystal Image, a 3×3 Gaussian blur was applied to reduce image noise, and a bi-level thresholding algorithm was applied to produce a binary segmented image such that onion bulb tissues were white and the background completely black. The threshold level was set to 30% of the maximum pixel intensity value in the image. In many cases, internal voids in the onion bulb also showed up as black, and Crystal Image's "Fill Holes" command was used so that a monolithic silhouette of the onion bulb was the only remaining image feature. Crystal Image's shape descriptors command was then run on this image, calculating the onion bulb silhouette's centroid, compactness, aspect ratio, irregularity, and Fourier shape descriptors.

The Fourier shape descriptors ($C_0 \ldots C_9$) for each onion specimen were imported into a spreadsheet, and each set of Fourier descriptors was normalized according to the mean radius ($C_0$) of each onion's silhouette. These normalized descriptors, $\zeta_1 \ldots \zeta_9$, have the advantage of being scale invariant, thus individual onion bulbs can be compared to one another. The mean value for the descriptors $\zeta_1$ through $\zeta_9$ was computed for all day 0 bulb cross-section images. This day 0 population average was used as a baseline against which to compare Fourier coefficients associated with scans of damaged bulbs.

Results (Hypodermic Inoculation):

*B. cepacia* proved to be the fastest-growing and most consistently damaging pathogen studied. Every one of the five bulbs inoculated exhibited internal (and in some cases, external) damage. *P. viridiflava*, in contrast, did not grow as readily when injected into onion bulbs and incubated in the laboratory. Incubation times were longer than those observed for *B. cepacia* and tissue damage tended to be more localized and subtle. In some samples, there was no detectable evidence of internal tissue damage caused by the bacterium after four weeks of incubation.

Figure 5:
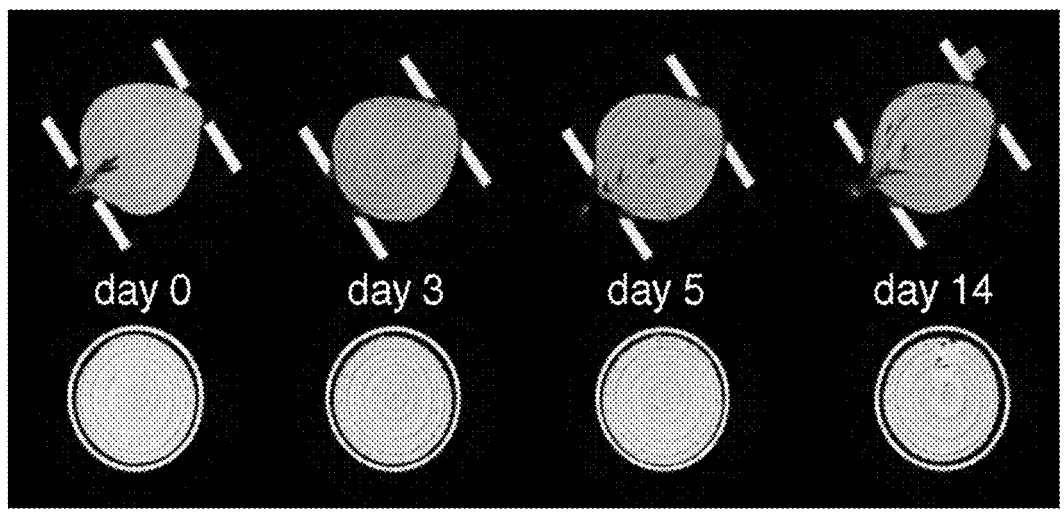
FIG. 5 is a digital image illustrating a first onion bulb inoculated with *B. cepacia*. The outer ring in the transverse images is due to the drinking cup holder used to secure the specimen to the scanner stage. Bacterial damage was not evident until day 14 and is not localized, but spread throughout the region near the injection site.

*B. cepacia* Images:

The first bulb injected with *B. cepacia* showed signs of damage after 14 days of incubation as shown in FIG. 5. Tissue damage was not localized to the internal regions of the onion bulb, but appeared to spread along the path the hypodermic needle took through the bulb. Dark regions can be seen in the day 5 transverse image, but whether these are due to bacterial decay or voids that arise as the onion tissues shift with changes in water content of the formation of leaf shoots is ambiguous.

Figure 6:
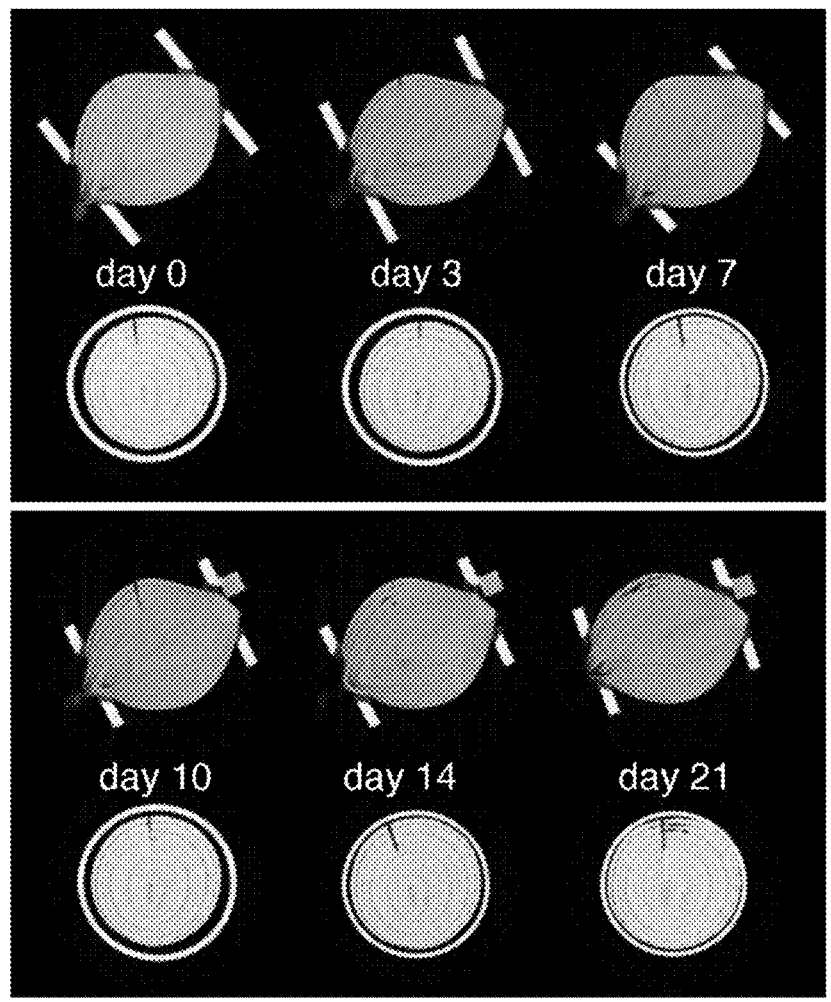
FIG. 6 is a digital image illustrating a second onion bulb inoculated with *B. cepacia*. The path of the hypodermic needle can be seen in transverse cross sectional images. Some small lesions can be seen in longitudinal images by day 10, and by day 21, large lesions can be seen in both projections near the injection site.

The second bulb inoculated with *B. cepacia* showed minor signs of damage after two weeks, and moderate damage after three weeks of incubation, as shown in FIG. 6. Gaps between the onion scales are evident in both transverse and longitudinal scans after 21 days.

Figure 7:
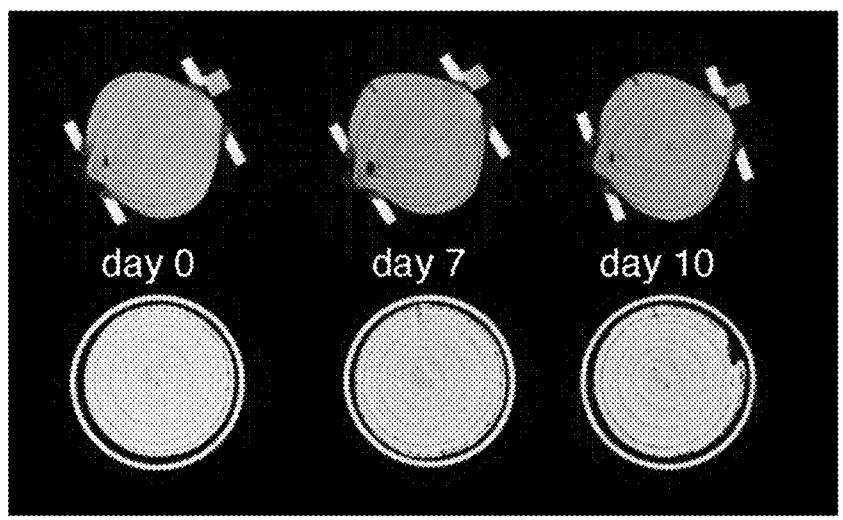
FIG. 7 is a digital image illustrating a third onion bulb inoculated with *B. cepacia*. Bacterial damage erupted seemingly overnight with this particular specimen.

One difficulty encountered in the study of *B. cepacia* infections is its growth pattern. The bacterium appeared to exhibit a latent period of several days before suddenly causing rapid and extensive damage to the inoculated bulb. This can be seen in the third onion bulb inoculated (FIG. 7). The bulb appears to be sound seven days after inoculation, but shows extensive damage only three days later. Like the first *B. cepacia*-inoculated bulb (FIG. 5), bacterial damage seems to have spread rapidly to the outer portions of the bulb, rather than growing in the interior. In the transverse scans of this particular bulb, a dark region can be seen near the neck end of the bulb that is likely due to natural variations in the lengths of the bulb's scales rather than pathogen damage, introducing more ambiguity to the analysis of these images.

Figure 8:
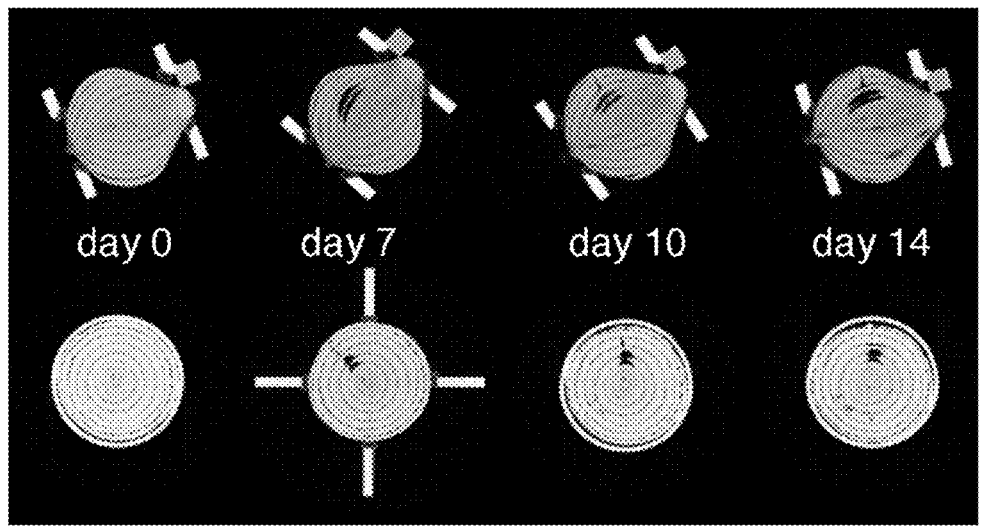
FIG. 8 is a digital image illustrating a fourth onion bulb inoculated with *B. cepacia*. The day 7 transverse image was obtained with a different, experimental specimen holder. Crescent-shaped damage features appear in both transverse and longitudinal cross sections as early as seven days after inoculation, though growth does not appear to progress in these areas in subsequent scans. By day 14, signs of decay are evident on the side of the bulb opposite the injection site.

The fourth bulb inoculated with *B. cepacia* showed signs of internal damage after only seven days, though the progression of this damage appears to have stalled until after two weeks of incubation, when additional lesions can be seen on the opposite side of the bulb from the inoculation site (FIG. 8).

Figure 9:
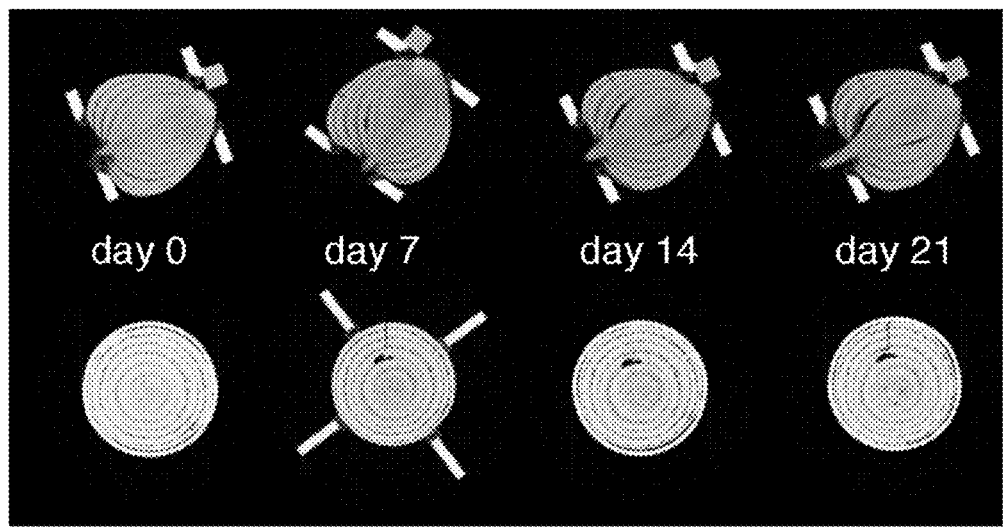
FIG. 9 is a digital image illustrating a fifth onion bulb inoculated with *B. cepacia*. This bulb began to sprout during incubation.
Figure 10A:
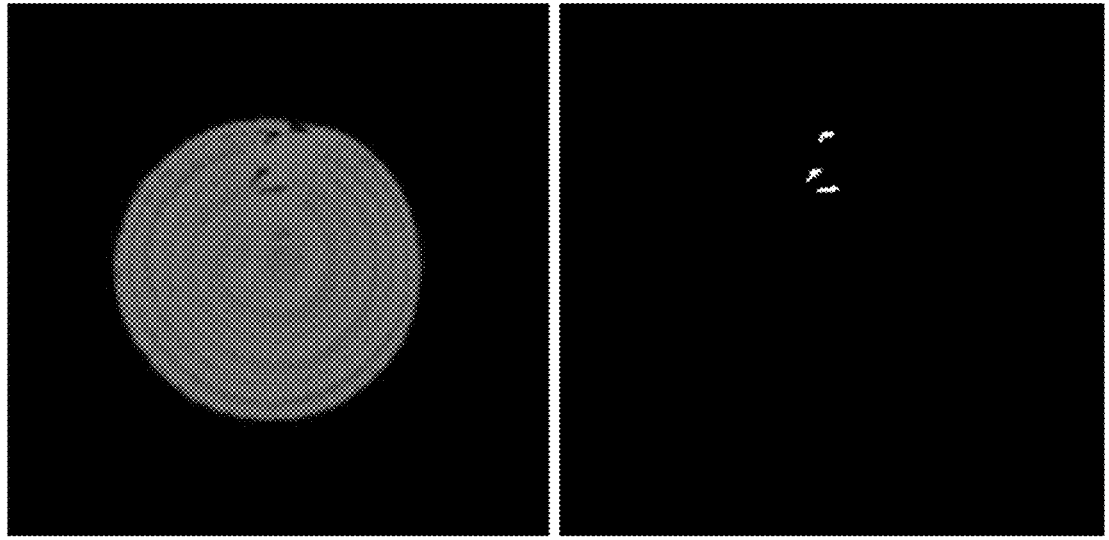
FIG. 10A is a digital image illustrating segmented features in the first *B. cepacia*-inoculated bulb. A few small dark spots were isolated near the injection site in this specimen, indicating the spread of the infection from this injection site.
Figure 10B:
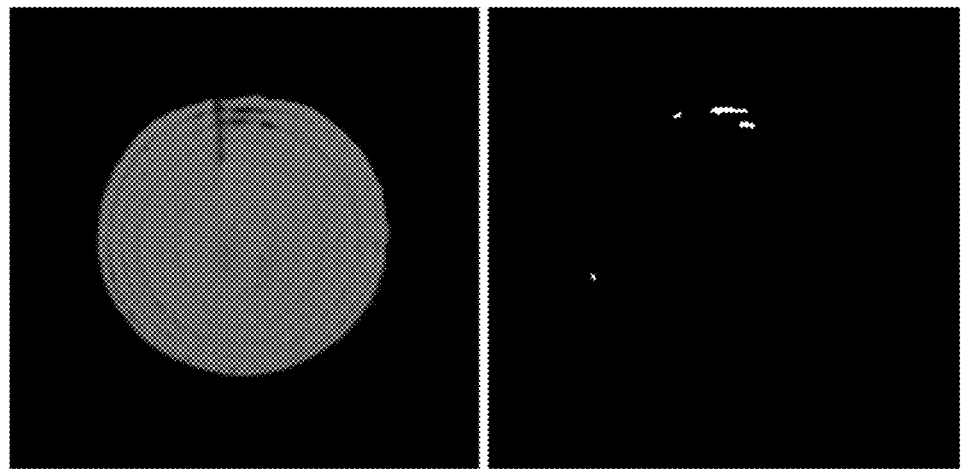
FIG. 10B is a digital image illustrating segmented features in the second *B. cepacia*-inoculated bulb. Again, the majority of the dark features segmented from the image appear near the pathogen's point of entry.
Figure 11:
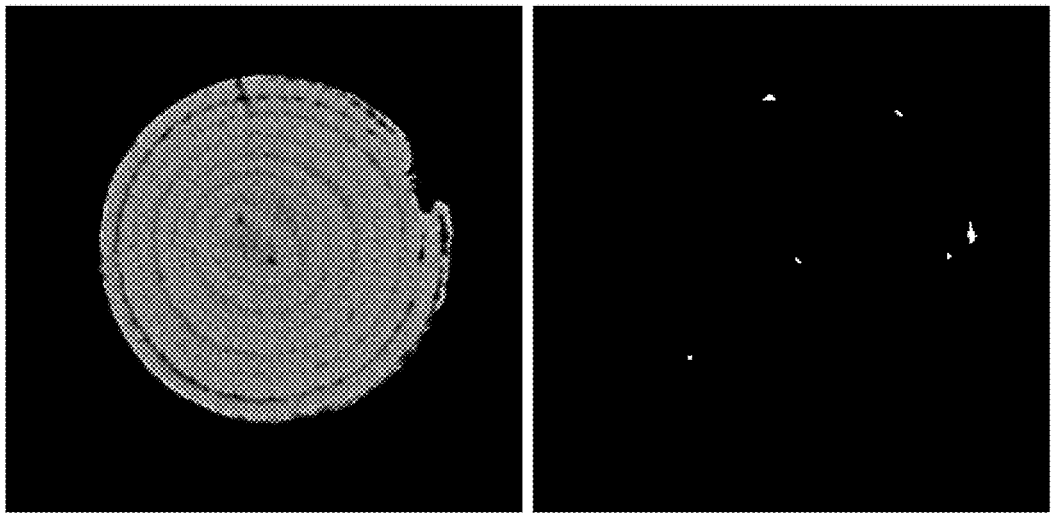
FIG. 11 is a digital image illustrating segmented features in the fourth *B. cepacia*-inoculated bulb.

The fifth and final *B. cepacia*-inoculated bulb showed the same early-stage damage as the fourth bulb (FIG. 9). An additional difficulty associated with image classification of onion CT images is illustrated in the longitudinal cross sections. A dark, crescent-shaped void could be seen developing near the neck of this bulb. However, by day 21, it can be seen that the bulb has grown leaf shoots, demonstrating that formation of such voids could also be due to deformation of the bulb's tissues as the shoots formed, rather than due to bacterial decay.

FIGS. 5-9 show the results of binary segmentation on the transverse cross section images. The first three specimens reveal relatively small dark spots near the outer edges of the bulb. A concentration of small dark spots localized to a specific portion of the bulb could be indicative of an active pathogen spreading from a single point of infection, whereas scattered, diffuse small lesions could emerge due to spaces between onion layers. On the fourth specimen (FIG. 8), a feature resembling two crescent shapes on top of each other is evident near the center of the bulb. The fifth specimen (shown in FIG. 9) has a single crescent shaped dark region near the center of the bulb. These features appear to indicate an infection spreading throughout one or two layers of onion tissue that is constrained within the already infected layers.

Figure 12:
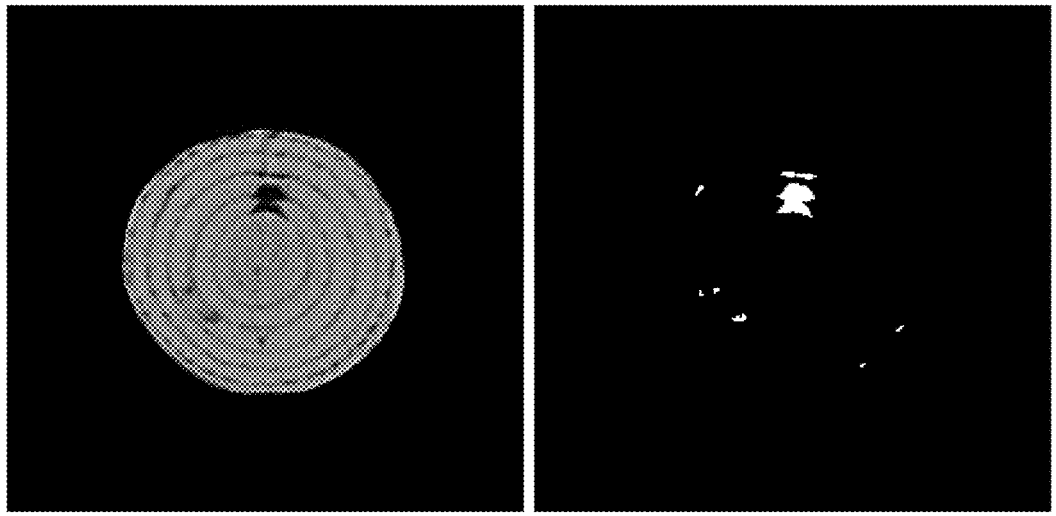
FIG. 12 is a digital image illustrating segmented features in the fourth *B. cepacia*-inoculated bulb.

Table 2 shows the size, compactness, aspect ratio, and irregularity values of the isolated features in the fourth bulb inoculated with *B. cepacia* and shown in FIG. 12. The high compactness values of the largest features indicate a large perimeter relative to the surface area of the feature. Such characteristics are highly unlikely to occur in healthy onion tissues and can be useful indicators of damage or morphological anomalies in onion tissues. In this particular specimen it appears that bacterial growth has progressed through two adjacent layers, traveling along their boundaries. The narrowing associated with the layer boundary in the largest damage feature has resulted in a much lower irregularity value for the feature, compared to the other segmented features.

TABLE 2

*B. cepacia* Infected Onion No. 4 Feature Characteristics

| Feature | Size (Pixels$^2$) | Size (mm$^2$) | Compactness | Aspect Ratio | Irregularity |
|---|---|---|---|---|---|
| 1 | 200 | 50.00 | 17.91 | 3.32 | 0.23 |
| 2 | 39 | 9.75 | 25.6 | 9.06 | 0.55 |
| 3 | 16 | 4.00 | 11.53 | 3.16 | 0.41 |
| 4 | 9 | 2.25 | 8.1 | 3.16 | 0.52 |
| 5 | 6 | 1.50 | 7 | 2.24 | 0.57 |
| 6 | 5 | 1.25 | 6 | 2.24 | 0.62 |
| 7 | 3 | 0.75 | 4 | 1.41 | 0.7 |
| 8 | 3 | 0.75 | 4 | 1.41 | 0.7 |

Figure 13:
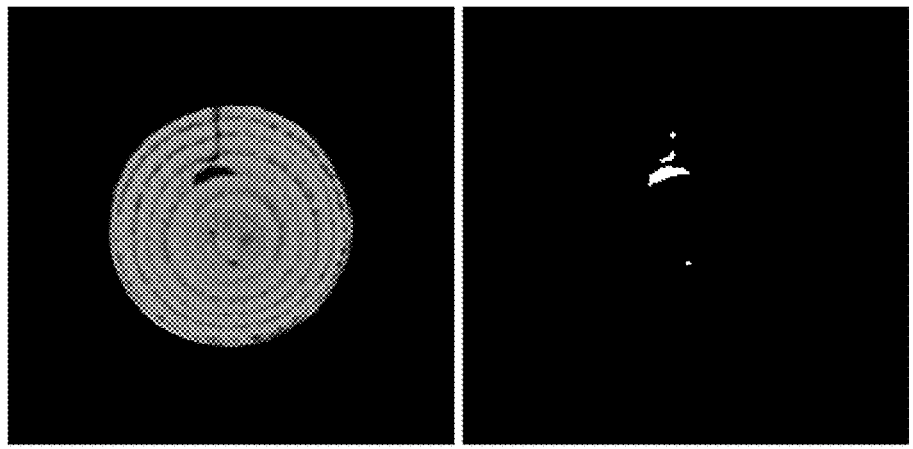
FIG. 13 is a digital image illustrating segmented features in the fifth *B. cepacia*-inoculated bulb.

As shown in FIG. 13, a large region of bacterial decay has been constrained to the interior of an onion layer near the center of the bulb. This large feature, whose characteristics are tabulated along with the other smaller features in Table 3, exhibits a relatively high compactness value. Unlike the large lesion seen in the fourth *B. cepacia*-inoculated bulb, the irregularity value of this feature is relatively high, owing to the smooth boundaries caused by the neighboring uninfected layers of the onion bulb.

TABLE 3

*B. cepacia* Infected Onion No. 5 Feature Characteristics

| Feature | Size (Pixels$^2$) | Size (mm$^2$) | Compactness | Aspect Ratio | Irregularity |
|---|---|---|---|---|---|
| 1 | 127 | 31.75 | 20.32 | 6.48 | 0.43 |
| 2 | 23 | 5.75 | 15.04 | 4.47 | 0.38 |
| 3 | 7 | 1.75 | 4.5 | 2 | 0.3 |
| 4 | 4 | 1.00 | 5 | 2.24 | 0.72 |

Figure 14:
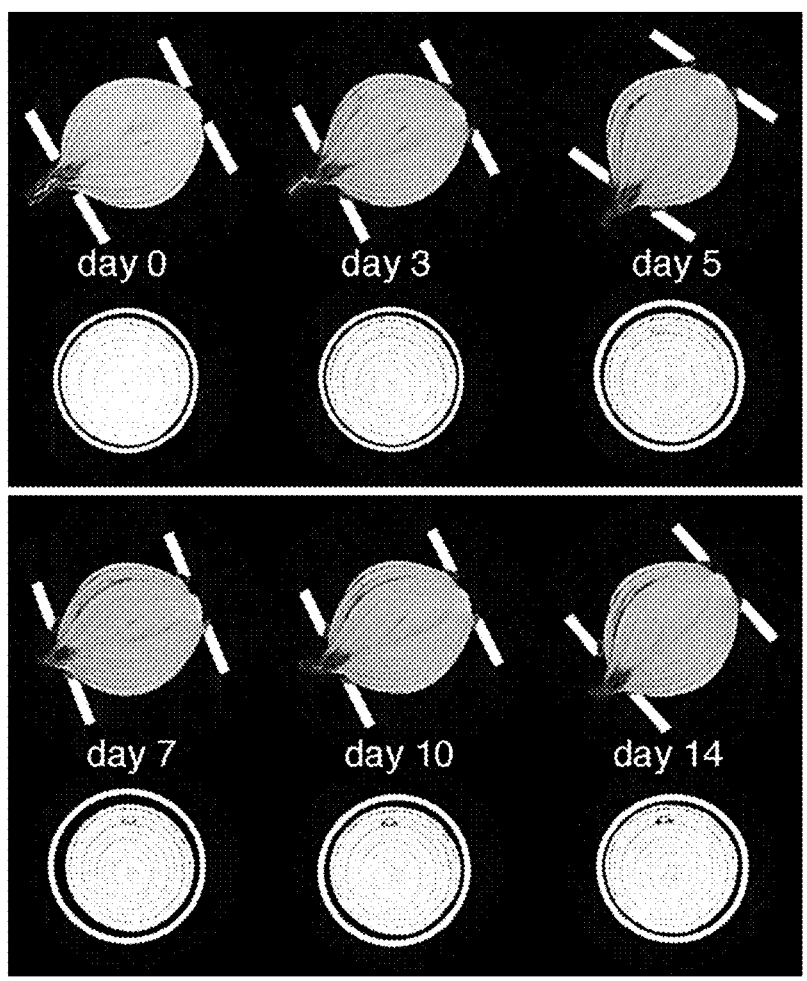
FIG. 14 illustrates the first bulb inoculated with *P. viridiflava*. Damage is evident after five days, and this damage slowly progresses over the course of subsequent scans.

*P. viridiflava* Images:

The first bulb inoculated with *P. viridiflava* exhibited signs of later separation in transverse cross section near the injection site, while transverse cross sections revealed small, round lesions, as shown in FIG. 14. Damage signs appear to be localized to the region surrounding the injection site, and the damage appears to progress at a slow and steady pace.

A second *P. viridiflava*-inoculated bulb showed little evidence of damage, even after 28 days of incubation (Figure \ref{fig:pv-02-progress}). Some small dark regions were seen in the vicinity of the injection site from day 7. However, several other small dark spots caused by natural variations in onion tissue density and vasculature were also evident in the images. The onion bulb began so sprout before any signs of extensive tissue damage were detected.

A third bulb inoculated with *P. viridiflava* also showed little, if any, evidence of bacterial damage. The most prominent dark regions in the cross sectional images of this bulb were due to variations in tissue structure and water content, not due to bacterial lesions.

Figure 15:
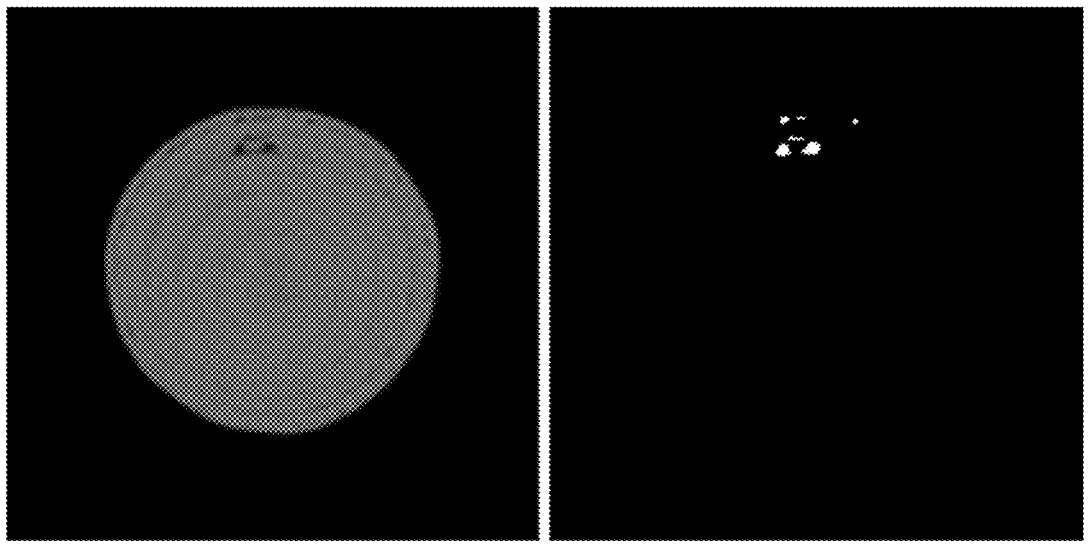
FIG. 15 illustrates the first bulb inoculated with *P. viridiflava*.
Figure 16:
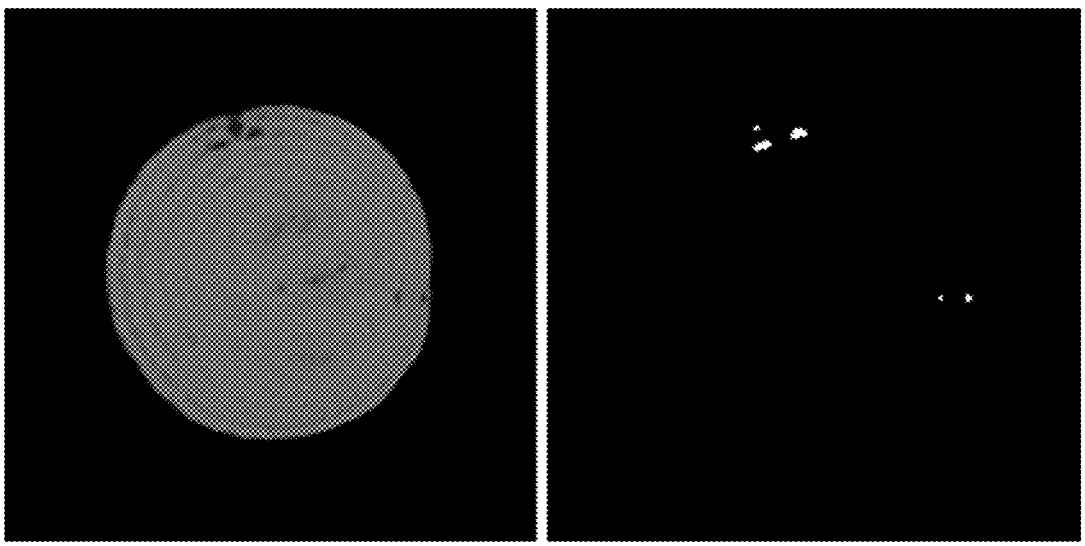
FIG. 16 illustrates the fourth bulb inoculated with *P. viridiflava*.
Figure 17:
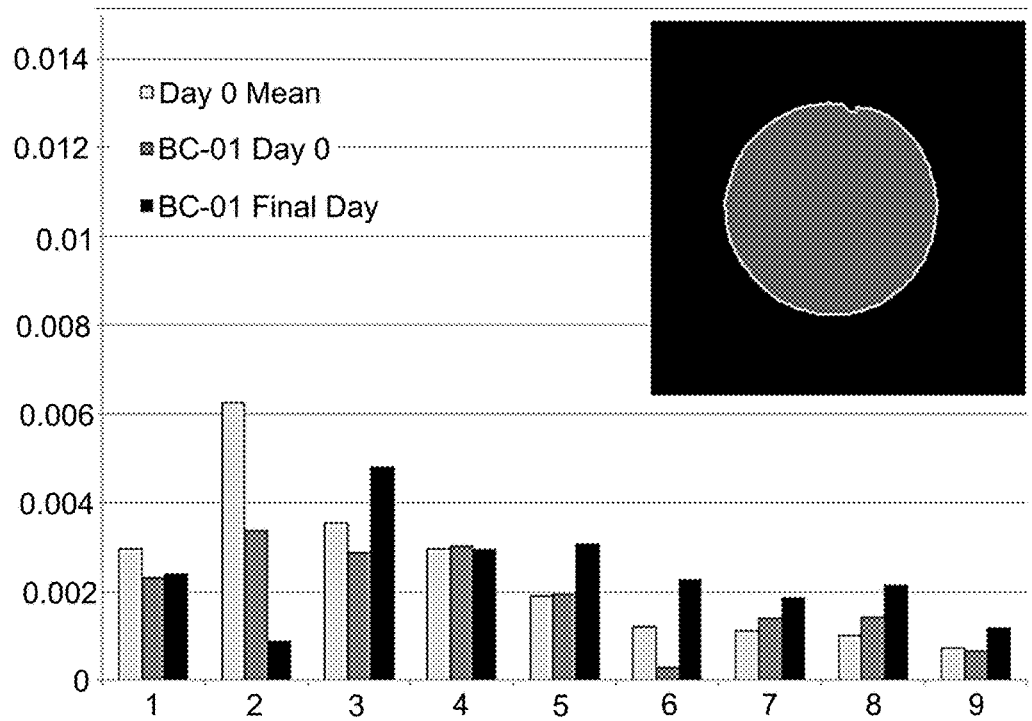
FIG. 17 is a graph illustrating the first bulb inoculated with *B. cepacia*. A small nick in the onion's surface can be seen at the top of the inset image. The values of $\zeta_5$-$\zeta_9$ show slight elevation compared the mean value for this population. Note that $\zeta_0$ is equal to 1, due to normalization, for all specimens, and is omitted in the charts.
Figure 18:
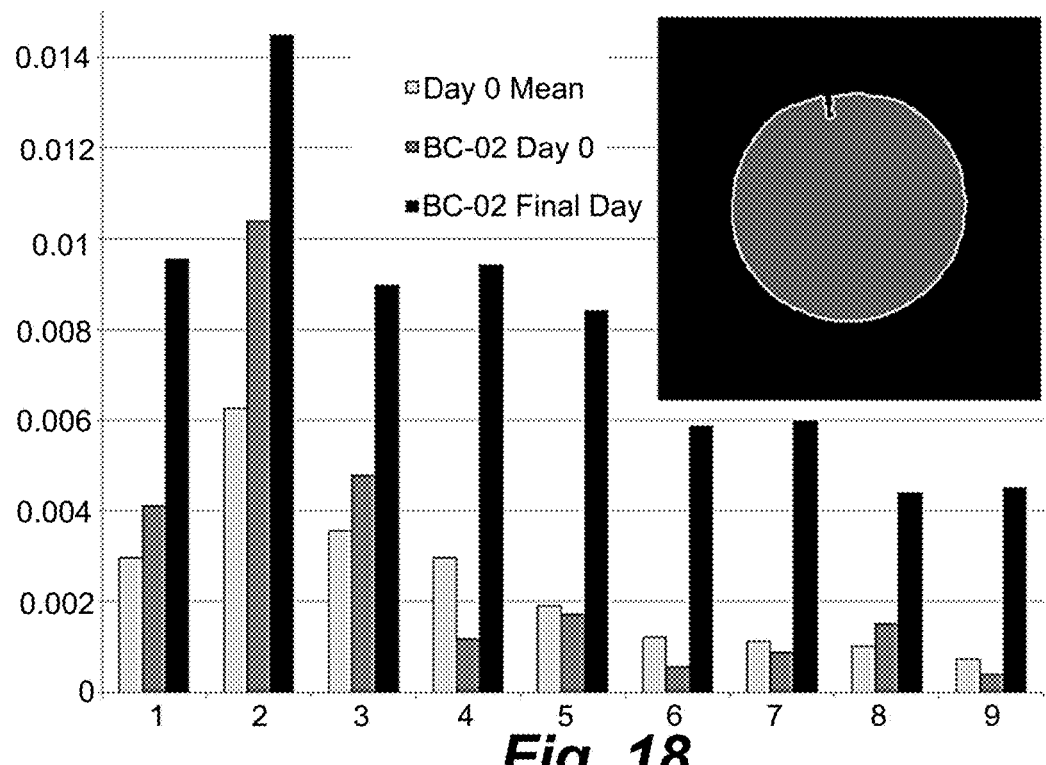
FIG. 18 is a graph illustrating the second bulb inoculated with *B. cepacia*. The particularly deep and narrow decayed channel in this specimen has led to large increases in all $\zeta$ values.
Figure 19:
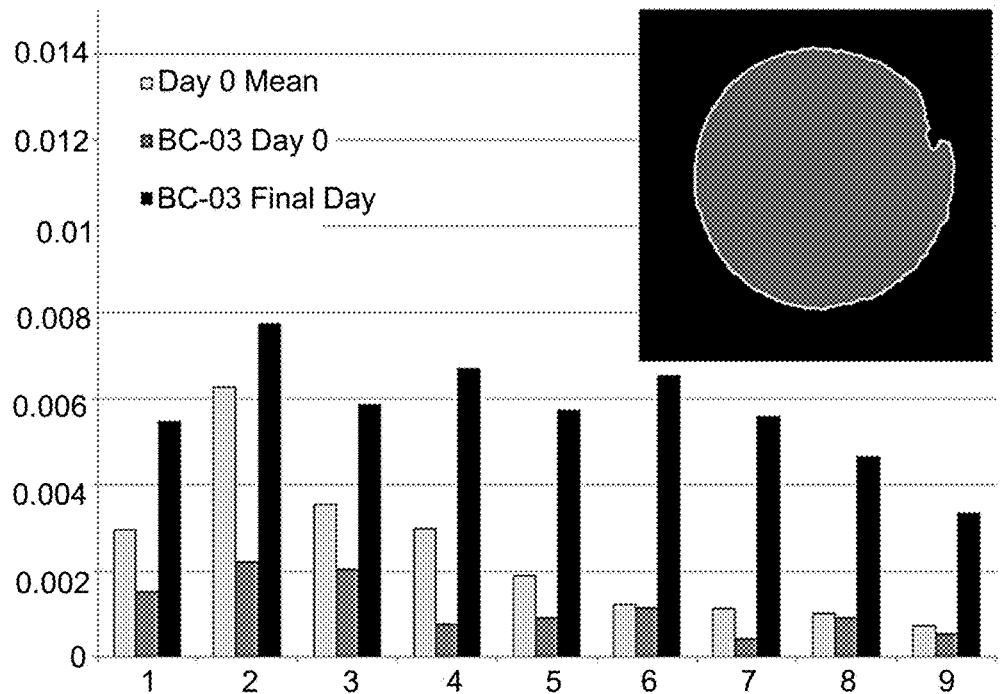
FIG. 19 is a graph illustrating the second bulb inoculated with *B. cepacia*. Again, extensive and deep surface damage lead to large increases in all $\zeta$ values.
Figure 20:
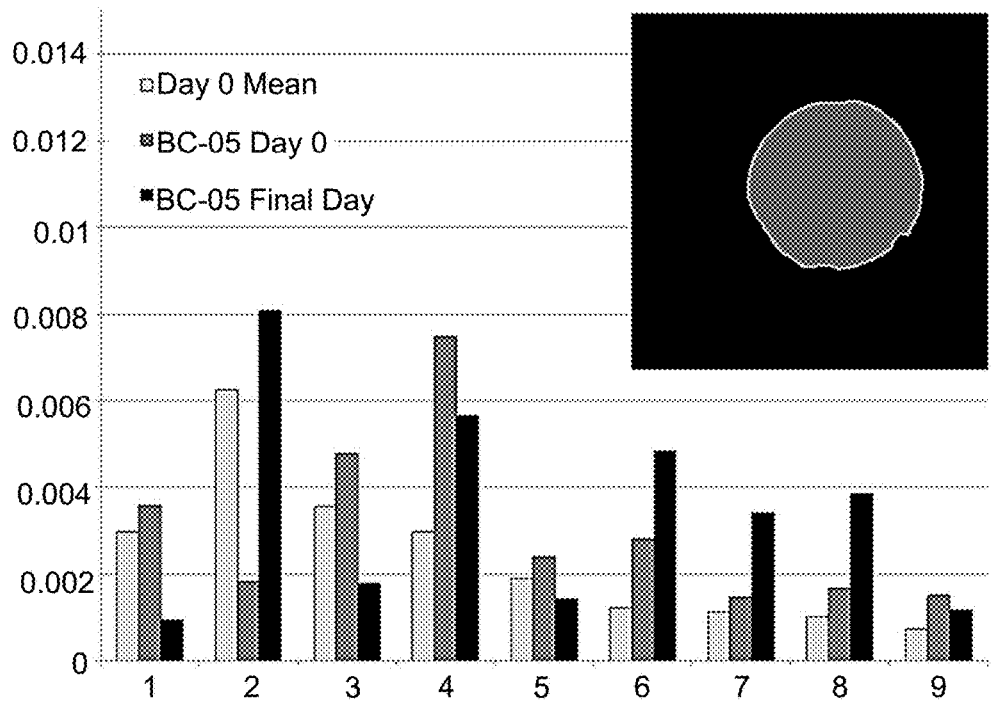
FIG. 20 is a graph illustrating the fifth bulb inoculated with *B. allii*. The damage to this specimen is more subtle than the others, but the two small dents at the bottom of the bulb have led to increases in value for $\zeta_6$, $\zeta_7$, and $\zeta_8$.
Figure 21:
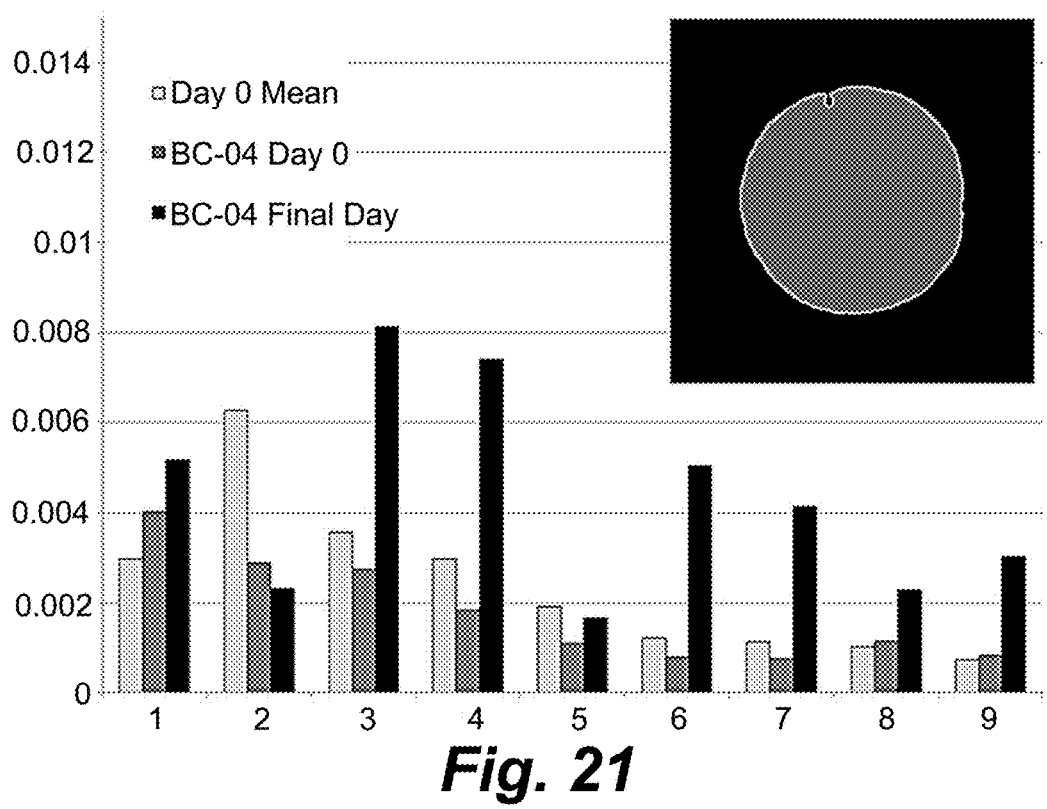
FIG. 21 is a graph illustrating the fourth bulb inoculated with *P. viridiflava*. Again, small, abrupt changes in the radius of the outer edge of the specimen relative to its centroid lead to large values for $\zeta_6$ through $\zeta_9$.

A fourth *P. viridiflava*-inoculated bulb (as shown in FIG. 15) showed signs of damage as early as day 7. Though this initial damage could have been caused by the inoculation of the bulb, rather than bacterial rot, the day 14 and day 21 transverse images show evidence of layer separation. This particular bulb also provided a demonstration of how capable CT imaging is of detecting multi-center onion bulbs. The transverse cross sections clearly show three sets of concentric rings, and the transverse cross sections show the emergence of three separate sets of shoots. Another feature of this specimen is the relative abundance of internal voids, compared to the single center bulbs that had heretofore been scanned. Such voids could provide an ideal environment for fungal or bacterial intrusion and growth, perhaps explaining the increased disease susceptibility associated with multi-center bulbs.

Only the first and fourth specimens inoculated with *P. viridiflava* showed any segmentable dark regions in transverse cross section images. In both cases, two small, round dark spots were isolated near the outer edges of the inoculated bulbs.

Fourier Shape Analysis:

Bulbs that exhibited signs of surface damage tended to have higher than average values for descriptors $\zeta_6$-$\zeta_9$ of their outlines, owing to the complex harmonics that are introduced to a Fourier transform of a parameterized curve when an abrupt change in radius is encountered. Oblong, ovoid shaped bulb cross sections exhibited higher than average values of $\zeta_2$ and $\zeta_3$, due to the contributions of the minor radii to the Fourier transform of the parameterized shape outline.

FIGS. 17-20 show plots of the day 0 mean $\zeta$ values for the population (14 specimens, total) alongside the individual's day 0 and final day $\zeta$ values. In all cases, elevations in some of the values of $\zeta_5$ through $\zeta_9$ can be observed, relative to both the initial population mean as well as each individual's day 0 values. The parameterized shape of each onion is displayed in an inset in each of these graphs to illustrate the effects of specific types of damage on Fourier $\zeta$ coefficients.

Though some undamaged bulbs may have larger day 0 values for some Fourier coefficients when compared to the population mean, in all cases, signs of damage led to increases in these same coefficients beyond the initial day 0 values. Thus, the larger C values relative to the mean for final day images can be attributed to malformation of the onion bulb's outer surface, and not to natural variation of healthy specimens.

Figure 22:
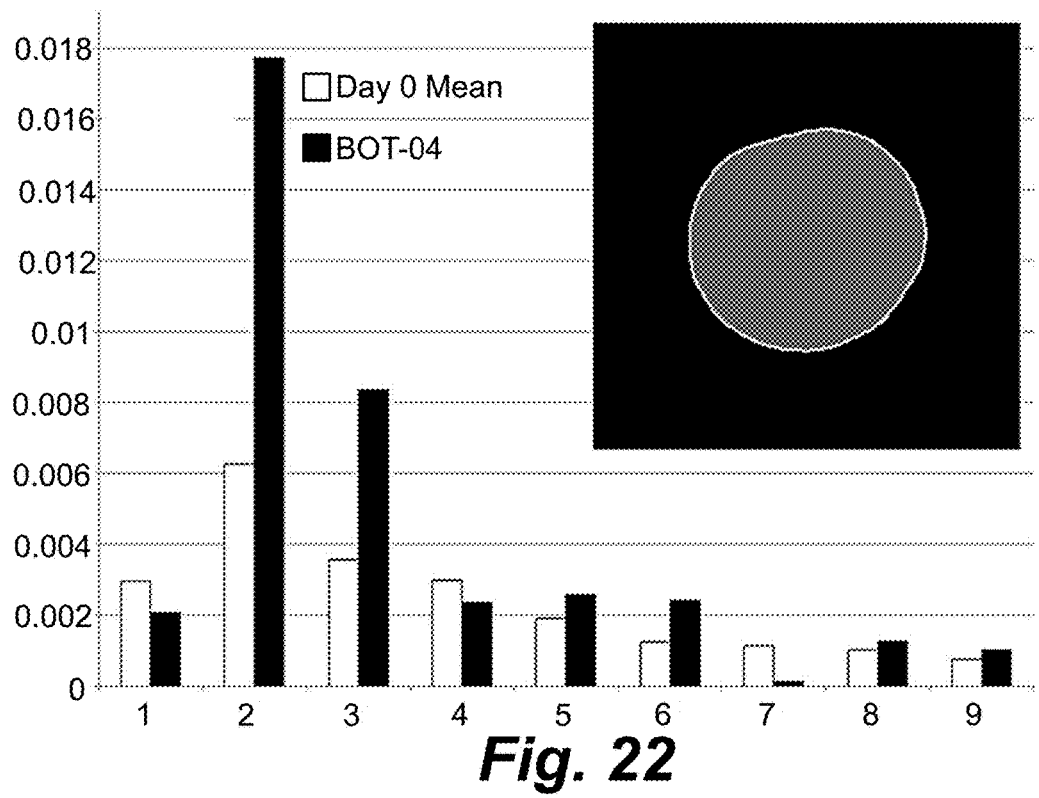
FIG. 22 is a graph illustrating the fourth bulb inoculated with *B. allii*. Though no signs of disease are present, the comparatively large values of $\zeta_2$ and $\zeta_3$ associated with this specimen demonstrate the ability of this analysis method in detecting misshapen ovoid bulbs.

FIG. 22 demonstrates the possibility of using Fourier analysis of onion outer edges as a quality control measure. This particular specimen exhibits a particularly ovoid shape, and its $\zeta_2$ value is particularly elevated. Such large elevations in $\zeta_2$ are indicative of elliptical shapes, and could be useful in screening out doubled bulbs.

Example 4

Onion Neck Inoculation:

Vidalia onions are particularly susceptible to *Botrytis* neck rot directly introduced to exposed onion neck tissues. All five of the sample onions inoculated exhibited signs of decay within a four week period. Peruvian-grown onions used in later experiments, by contrast, exhibited less sensitivity to neck-based inoculation of the pathogens.

*Botrytis*-Inoculated Vidalia Onions:

In general, the longitudinal cross section images appeared to provide more useful information regarding the spread of *Botrytis* neck rot, though this was largely due to the location of the scan sites relative to the actual location of the infection. It was initially believed that as the infection spread downward from the onion's neck towards its root end, it would eventually intersect the transverse cross sectional plane and reveal characteristic damage patterns. While this appears to have occurred in a few of the images, detection of rot-induced damage is complicated by the formation of leaf shoots which can cause internal voids and localized low-density regions near the center of the bulb.

Figure 23:
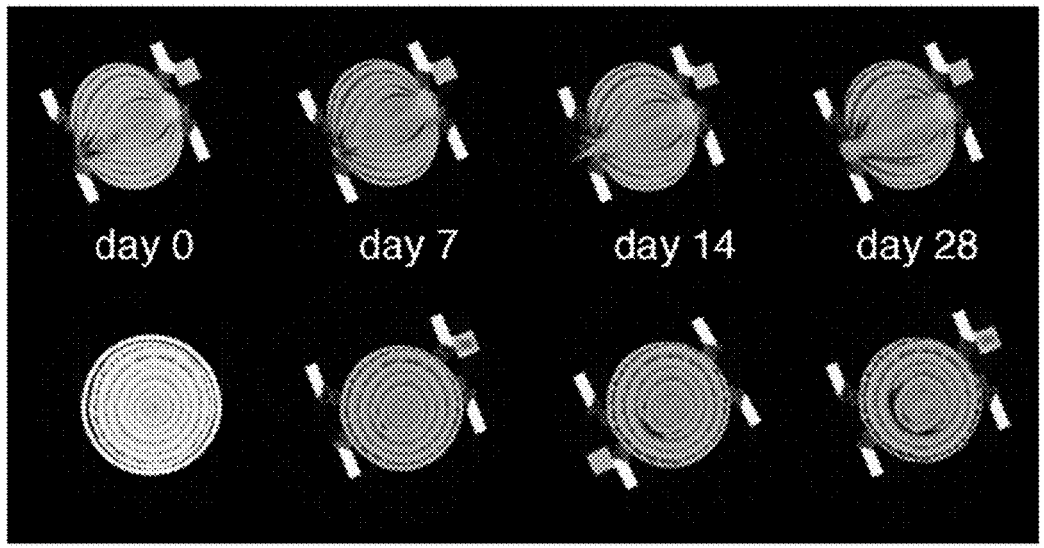
FIG. 23 illustrates the first *Botrytis*-inoculated Vidalia onion. Damage is evident by day 14 in the transverse image, where the fungal rot has been traveled down a single layer. In longitudinal cross section, the ends of the layers near the neck of the onion have begun to darken by day 28.

The transverse images of the first *Botrytis*-inoculated bulb, as shown in FIG. 23, revealed signs of decay in one of the internal layers after fourteen days of incubation, and this decayed region increased in size in the subsequent transverse scan two weeks later. Longitudinal scans revealed darkening of the ends of the onion bulb scales near the neck, and these dark regions increase in length along the scale outlines as the disease progresses. Some layer separation was evident, as the onion began to sprout during incubation, leading to the formation of voids between the actively growing shoots and the outer bulb scales.

The second bulb inoculated with *Botrytis* showed clear signs of damage in the final transverse cross sectional image. Several irregularly-shaped voids appear near the neck end of the bulb, and the tissue surrounding these voids appears deformed. The final transverse cross section image could also show evidence of damage; there are definite dark regions and voids, though this onion bulb began sprouting during incubation, so some of these dark regions could be attributed to morphological changes that occur as the shoots begin to emerge.

The third bulb inoculated with *Botrytis* showed clear, unambiguous evidence of internal rot in both transverse and longitudinal cross section. Early images show evidence of internal shoot formation and the accompanying dark voids that occur as the shoots grow. By day 14, the transverse image showed some light gray regions forming along the ends of the scales. The final transverse image showed the tissue deformation and dark voids that result as the infection is allowed to progress. The final transverse cross section image showed a thoroughly irregular and disordered inner core.

The fourth bulb inoculated with *Botrytis* had decayed so thoroughly by day 28 that it could no longer be reliably held in the specimen holder for imaging. The bulb rot progressed rapidly between day 14 and 28; there was slight evidence of decay at the ends of the bulb scales in the day 14 longitudinal image, but the bulb had clearly completely rotted by day 28. Secondary infections could account for the more rapid decomposition of this particular specimen.

The fifth bulb inoculated with *Botrytis* began to exhibit signs of sour skin infection as well as neck rot after two weeks of incubation. Slight decay of the outer skin could be observed in the transverse image from day 14. By the following week, the bulb decay was so advanced that it could not be placed in a holder for imaging. Again, the longitudinal cross section images showed a darkening of the neck-end scales of the bulb, indicating that the *Botrytis* infection is spreading downwards toward the center of the onion, leaving decayed tissues behind.

Figure 24:
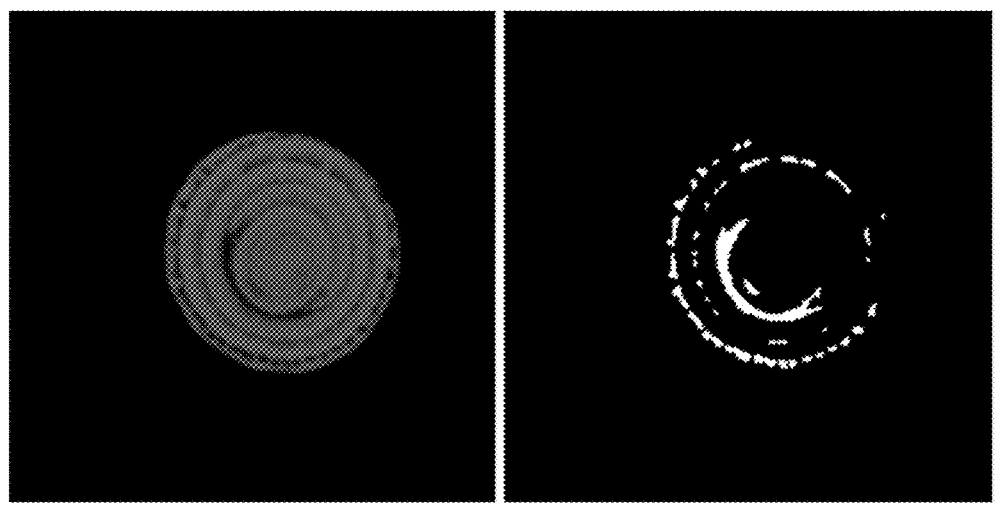
FIG. 24 shows the segmented features in the first *Botrytis*-inoculated onion.

FIG. 24 shows a representative result of segmentation of the transverse cross sectional images of inoculated and incubated onions after binary image value segmentation. Cluster analysis was conducted on the resultant isolated image features, and the characteristics of these features found in the first, second, and third *Botrytis*-inoculated onions are listed in Table 4. The third and fourth onions inoculated with *Botrytis* exhibited only small dark regions that, while possibly caused by infection, could not be reliably distinguished from natural variation within onion tissues or image noise.

After segmentation, the first three specimens exhibited numerous small features in addition to a few larger features. While an abundance of small dark regions could be indicative of bacterial or fungal infection, the larger features were regarded as more reliable indicators of infection. These larger features tended to exhibit high compactness values compared to the other features. Such values are indicative of large and branching areas that are highly unlikely to occur naturally in onion tissues, making them good indicators of damage to the bulbs. Small features, on the other hand, are more difficult to characterize in terms of compactness and regularity, as the resolution of the images becomes a limiting factor in the calculation of these characteristics.

TABLE 4

*Botrytis* Onion No. 1 Feature Characteristics

| Feature | Size (Pixels$^2$) | Size (mm$^2$) | Compactness | Aspect Ratio | Irregularity |
|---|---|---|---|---|---|
| 1 | 600 | 150.00 | 83.49 | 4.36 | 0.35 |
| 2 | 61 | 15.25 | 17.56 | 7.81 | 0.46 |
| 3 | 47 | 11.75 | 27 | 9 | 0.55 |
| 4 | 47 | 11.75 | 15.19 | 8.6 | 0.52 |
| 5 | 47 | 11.75 | 16.33 | 7.28 | 0.49 |
| 6 | 45 | 11.25 | 25.13 | 10.44 | 0.58 |
| 7 | 45 | 11.25 | 13.59 | 7.21 | 0.5 |
| 8 | 44 | 11.00 | 21.36 | 8.06 | 0.49 |
| 9 | 39 | 9.75 | 24.02 | 9.9 | 0.58 |
| 10 | 36 | 9.00 | 13.08 | 6.4 | 0.46 |

The first *Botrytis*-inoculated bulb's most prominent feature was the crescent shaped region near the center. Such crescent shapes appear as fungal infection spreads through and decays a single layer of the onion without affecting the surrounding layers. The overall curvature of the shape leads to a relatively low aspect ratio, even though the damage occurs in a narrow channel within the onion. The compactness value, however indicated a feature that has a long outer perimeter compared to its surface area. The low irregularity value arises as the edges of the damage feature are bordered mostly by healthy onion layers which exhibit smooth edges.

TABLE 5

| Feature | Size (Pixels$^2$) | Size (mm$^2$) | Compactness | Aspect Ratio | Irregularity |
|---|---|---|---|---|---|
| 1 | 48 | 12.00 | 13.8 | 7.07 | 0.42 |
| 2 | 44 | 11.00 | 21.36 | 9.22 | 0.51 |
| 3 | 27 | 6.75 | 20.57 | 7.07 | 0.52 |
| 4 | 15 | 3.75 | 16 | 5.1 | 0.51 |
| 5 | 15 | 3.75 | 9 | 3.61 | 0.44 |
| 6 | 14 | 3.50 | 9.6 | 3.61 | 0.44 |
| 7 | 9 | 2.25 | 10 | 2.83 | 0.51 |
| 8 | 7 | 1.75 | 8 | 2.24 | 0.55 |
| 9 | 7 | 1.75 | 8 | 2.24 | 0.55 |
| 10 | 3 | 0.75 | 4 | 1.41 | 0.7 |

The features isolated in the second *Botrytis*-inoculated onion were relatively small compared the ones in the first onion. The features near the outer edge of the bulb were likely natural dark spots that appear in the more dried outer layers of the bulbs, and the features closer to the center could be caused either by shoot formation or fungal decay. Discrimination between healthy tissues and damage was difficult in this particular specimen, as none of the features exhibits notably high or low compactness, aspect ratio, or irregularity values.

TABLE 6

*Botrytis* Onion No. 3 Feature Characteristics

| Feature | Size (Pixels$^2$) | Size (mm$^2$) | Compactness | Aspect Ratio | Irregularity |
|---|---|---|---|---|---|
| 1 | 660 | 165.00 | 152.03 | 3.46 | 0.29 |
| 2 | 169 | 45.25 | 29.65 | 16.12 | 0.47 |
| 3 | 55 | 13.75 | 19.45 | 10 | 0.49 |
| 4 | 37 | 9.25 | 11.61 | 5 | 0.33 |
| 5 | 37 | 9.25 | 13.92 | 6.08 | 0.42 |
| 6 | 33 | 8.25 | 19.88 | 6.4 | 0.49 |
| 7 | 29 | 7.25 | 13.33 | 5.1 | 0.43 |
| 8 | 28 | 7.00 | 15.21 | 5.1 | 0.48 |
| 9 | 24 | 6.00 | 25 | 8.54 | 0.59 |
| 10 | 22 | 5.50 | 11.13 | 4.12 | 0.46 |

This bulb displayed extensive internal damage. The largest damage features, upon segmentation of the image, became connected, forming an especially large cluster with a high compactness value. Nevertheless, the irregularity of this feature is low, as the fungal decay is still constrained to specific layers within the bulb.

The fourth and fifth bulbs inoculated with *Botrytis* showed no visible signs of decay in transverse cross section. The isolated features that emerge after binary segmentation are naturally occurring dark spots that sometimes appear between the layers. These features are characterized by their small size, and an automated quality evaluation system should only evaluate features above a set size threshold.

Figure 25:
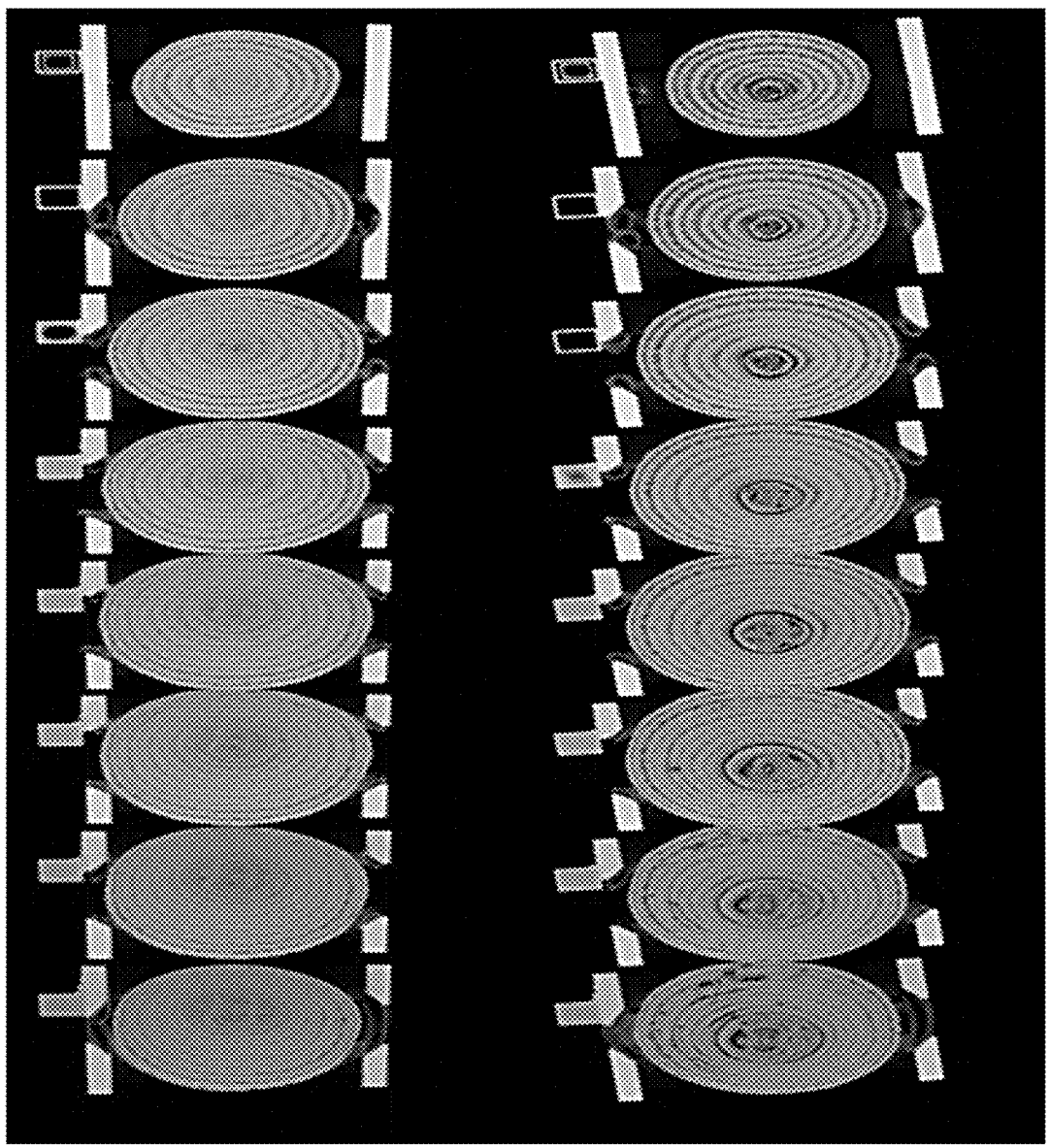
FIG. 25 shows the seventh *B. cepacia*-inoculated onion. Extensive damage is evident after five weeks of incubation, though the damage lesions appear near the root end of the bulb, rather than in the vicinity of the site of inoculation.

Three-Dimensional Images:

The pathogens did not grow as readily in the set of Peruvian-grown sweet onions as they did in the Georgia-grown Vidalia onions, likely owing to the greater disease resistance of the Peruvian onions. In several cases, onions were incubated for such a long period that their newly exposed necks dried out, leading to dark, low density regions in the CT images that are difficult to discern from damage caused by actual pathogen growth. One onion inoculated with *B. cepacia* exhibited signs of infection, one onion inoculated with *B. allii* exhibited signs of infection, and none of the onions inoculated with *P. viridiflava* displayed any signs of infection. A representative 3D-scanned onion bulb is shown in FIG. 25. Slices from initial, pre-inoculation scans are shown on the left-hand side of the figures, and slices from the final scans (when bulbs show signs of pathogen damage, or at the end of the study period) are shown on the right-hand side. The slices, as shown for example in FIG. 25, were presented in oblique view to show internal structure as well as spatial arrangement, though the interslice spacing has been enhanced to prevent slices from overlapping and occluding each other.

Figure 26:
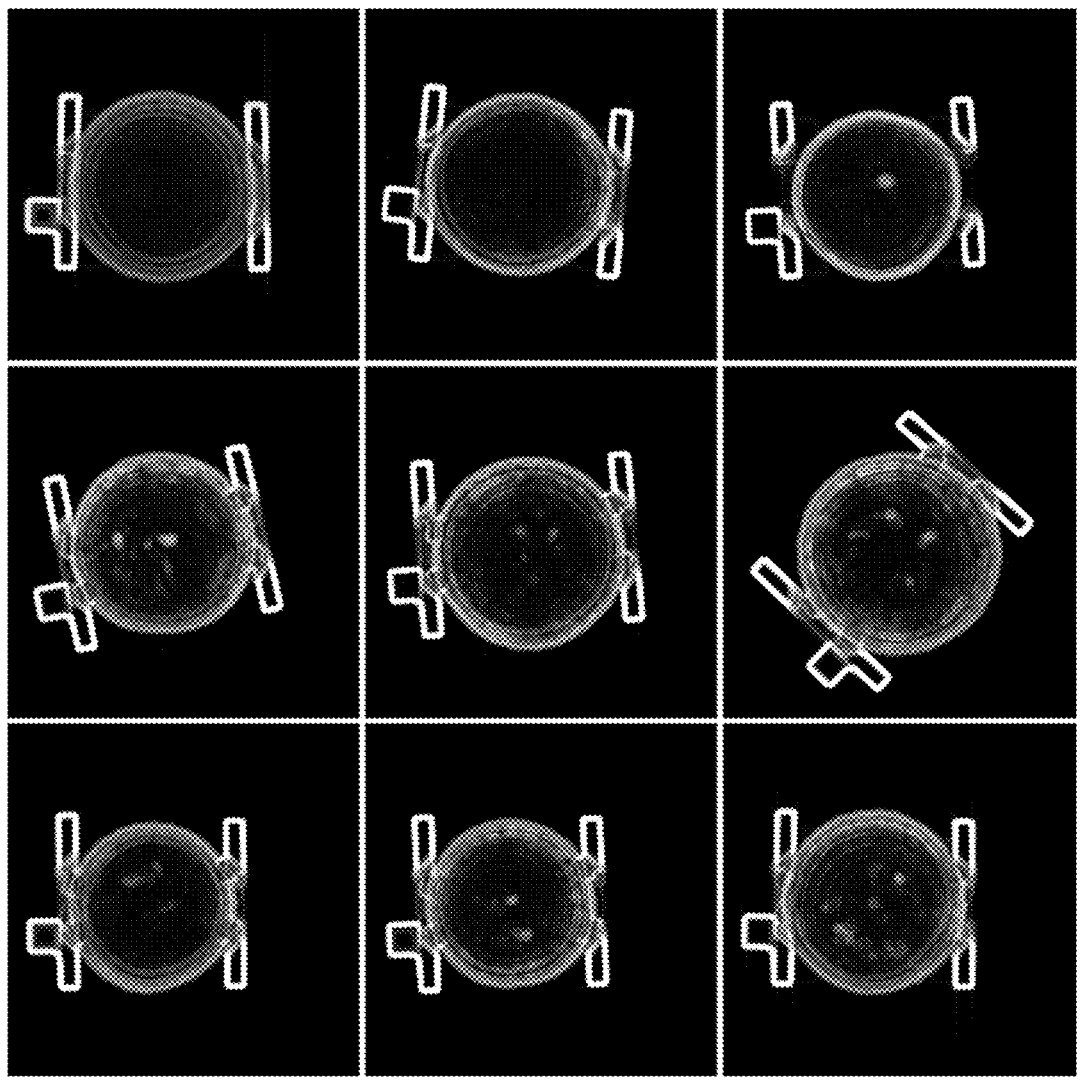
FIG. 26 shows average intensity $\zeta$-projections of transverse cross section image stacks after a 1-pixel variance filter. The bulbs in the upper left and upper middle panels have single centers and the other bulbs have two or more centers. Small, localized regions near the center of the bulb exhibiting high variance are indicative of air gaps that occur between multiple onion centers.

Multicenter Bulb Detection:

Though the Peruvian sweet onions did not readily grow pathogens in the laboratory setting, they did exhibit other attributes that can be useful in the development of a CT-based onion quality control protocol, namely multiple centers. All but two of these nine specimens had at least two centers. In the transverse cross sectional images, regions in which multiple centers collide tend to exhibit small, dark air gaps where the curvature of the onion scales will not fill the space. These air gaps were identified by computing a 3×3 pixel local variance of each slice. This operation effectively enhanced small image features in which there was great contrast between the feature and its surroundings, such as these air gaps between onion centers and the outline of the onion bulb against the black background. FIG. 26 shows the results of running this 3×3 variance on each onion slice and recombining the slices via a mean value Z-projection. The single center bulbs display a relatively homogeneous internal texture, whereas the air gaps associated with multiple centers show up as bright regions near the center of bulbs with multiple centers.

Example 5

Onion Bruising:

FIGS. 27-31 show longitudinal and transverse cross sections of the bulbs dropped onto hard concrete. The first column in each figure shows cross sectional images of the onion bulb as received, prior to any laboratory-induced impact damage. The center column in each figure shows the onion bulb immediately after being dropped. Finally, the right-hand column shows the onion bulb three days after being dropped.

Evidence of damage becomes more prominent after the onions have been stored for a period of time. Longitudinal images of the two bulbs dropped from 70 cm and 105 cm show slight signs of damage immediately after being dropped, though these signs are subtle and illustrates that it would be difficult to devise an automated system that would be able to discern such damage from natural variation inside the onion tissues without a priori knowledge that the bulb had been subjected to impact damage.

Figure 27:
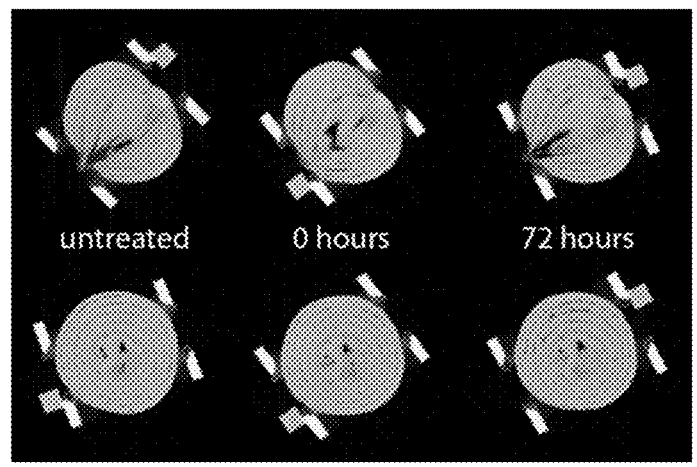
FIG. 27 illustrates a CT scan of an onion dropped six times from a height of 17.5 cm.

The bulb dropped repeatedly from 17.5 cm, as shown in FIG. 27 exhibits characteristic damage patterns within its inner scales. Jagged, irregular dark regions appear inside the scales, but these features end where they coincide with the dark boundary regions between the scales. Thus, if these dark scale boundaries are traced, the interior edge (facing inward, towards the center of the onion) continues smoothly as in a healthy onion, whereas the outer edge exhibits jagged and irregular regions. This observation applies to the longitudinal images as well as the transverse images.

Figure 28:
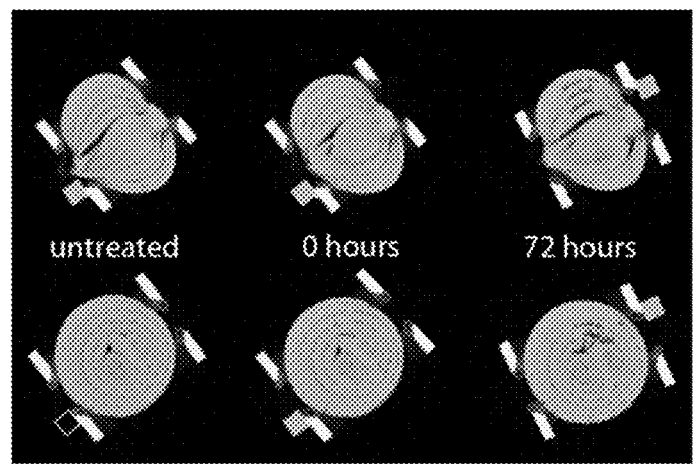
FIG. 28 illustrates a CT scan of an onion dropped six times from a height of 35 cm.

As shown in FIG. 28, a bulb dropped from 35 cm also exhibits these characteristic damage patterns. Additionally, in the transverse image, it appears that the impact has caused one of the inner scales to split completely in half.

A bulb dropped from 70 cm exhibits some of the characteristic damage features observed in the bulbs dropped from shorter heights, though in its outer scales, the interscale dark regions have disappeared. Such high impact forces apparently caused such substantial damage to the scales that they could no longer be clearly discerned, perhaps due to fluid leakage filling these interlayer gaps. This effect could be seen in the images obtained immediately after the drop treatment, as the dark spaces between the scales merge together near the impact site, whereas they were easily followed in the pre-treatment images.

A bulb dropped from 105 cm exhibited the damage patterns seen in specimens dropped from lesser heights. However, the merging of the interlayer gaps was less prominent immediately after treatment than in a bulb dropped from 70 cm.

Images were reconstructed from 140 kVp sinograms using Crystal Image v.0.9.5, negative pixel intensity values that remained as artifacts of filtered back projection reconstruction were clipped to zero, and images were saved as 32-bit signed floating point grayscale TIFF image files. These 32 bit images were then batch converted to 16 bit images via a custom-designed program written in the C programming language.

Transverse cross section images were opened in the Mac OS X version of NIH ImageJ v.1.46r, and ImageJ's Threshold operator was used to segment the images by pixel intensity value. Threshold values were chosen manually and subjectively, and these thresholds varied from image to image. After segmentation, onion tissues and the specimen holder appeared as white features on a black background, with some black low density features inside the white onion shape. Specimen holder features were manually selected by enclosing them with a polygon selection tool, and these selections were filled with black, thereby leaving only the onion and its low density features in the image. This segmented image was then saved as a grayscale PNG file.

The centroid of the overall onion shape was obtained by filling all the black low density features inside the onion's silhouette with white, and using ImageJ's 'Analyze Particles' command. The pixel area of the shape as well as the x and y coordinated for its centroid were recorded. The segmented PNG files were then reopened, and the dark low density regions inside the onion were isolated by inverting the pixel values so onion tissues were black on a white background. This white background was then flood filled with black, leaving only the low density internal onion features as white shapes on a black background. The pixel values were the inverted again, and ImageJ's 'Analyze Particles' command was executed, reporting the x and y centroid values, pixel area, aspect ratio, circularity, and solidity of each contiguous block of white pixels. These values were exported to a Microsoft Excel file for further analysis.

A weighting system was devised that would give preference to low density features farther from the center of the onion, as these features were deemed to be most likely caused by bruise damage, whereas low density features near the center of the onion were more likely to be due to emergent shoots or damage caused by infections. Feature data were loaded into Microsoft Excel:Mac 2011, and each low density pixel cluster's distance from the centroid of the overall onion shape was calculated. Each cluster's distance from the centroid was normalized by the maximum feature distance detected in the image, and this normalization was squared. Therefore, the maximum normalized squared distance weighting factor in the image is 1, which corresponds to the most distant feature, and features near the center of the onion bulb have weighting factor values less than 1. Each weighting factor was then multiplied by the pixel area of the corresponding feature, yielding a weighted damaged area metric. the weighted damage area metric is described by the equation:

$$\text{Weighted Damage Area} = a \cdot \left(\frac{d}{d_{max}}\right)^2$$

where a is the area of the individual cluster, d is its distance from the onion centroid, and $d_{max}$ is the distance between the onion centroid and the most distant cluster. If the weighted damaged area of a given cluster exceeds a pre-determined threshold value it is considered part of a bruise; features whose weighted damaged area values are beneath the threshold are not considered bruise damage.

Finally, an additional metric was developed to determine the localization of bruise damage in an onion bulb and to prevent spurious, naturally occurring, low density regions in the onion bulb from being considered in damage estimation of a bulb. Bruise damage features appear to cluster around the center of impact, so closely clustered damage features are more likely to be caused by bruising than features that are spread throughout the bulb. A weighted center of mass function was devised to accomplish these goals. Each damage feature is assigned a weighting factor consisting of its normalized distance from the onion centroid multiplied by the pixel area of the feature. Each feature's weighting factor is then multiplied by its x and y coordinates. The weighted x and y coordinates are summed, and these sums are divided by the sum of the weighting factors to obtain the weighted center of mass for the damage features. how the x-coordinate for the weighted center of mass is calculated is shown by the equation:

$$x_{weighted} = \frac{\sum_{n=1}^{m}\left(x_n \cdot a_n \cdot \frac{d_n}{d_{max}}\right)}{\sum_{n=1}^{m}\left(a_n \cdot \frac{d_n}{d_{max}}\right)}.$$

for an image exhibiting m low density clusters, where $x_n$ is the x-coordinate of cluster n's centroid, $a_n$ is cluster n's pixel area, $d_n$ is the distance of cluster n from the onion's centroid, and $d_{max}$ is the maximum distance between a cluster and the onion's centroid. This process is repeated for the y-coordinates, and the resultant x,y coordinate is the estimated center of damage in the onion bulb. Standard deviations for the weighted x and y coordinates are calculated, and damage features whose centers fall outside one or two standard deviations from the weighted center of mass can be excluded from consideration. Specimens exhibiting widely distributed, large sized low density features would have high standard deviations, and such specimens would likely have extensive damage, rendering them unsalable.

Figure 29:
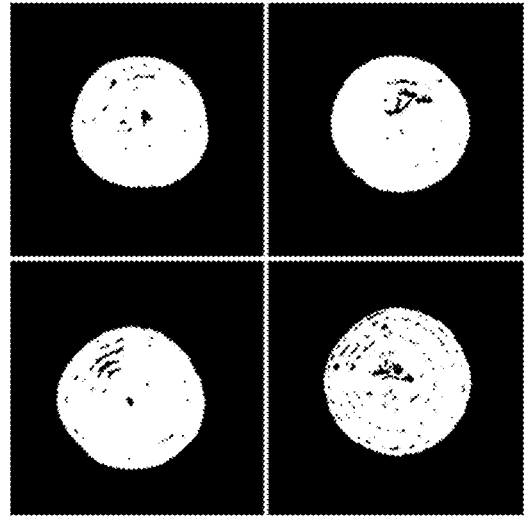
FIG. 29 illustrates transverse cross sectional images of drop-tested onions after segmentation and removal of specimen holder. Top Left: Onion dropped six times from a height of 17.5 cm. Top Right: Onion dropped six times from a height of 35 cm. Bottom Left: Onion dropped twice from a height of 70 cm. Bottom Right: Onion that was dropped once from 105 cm.
Figure 30:
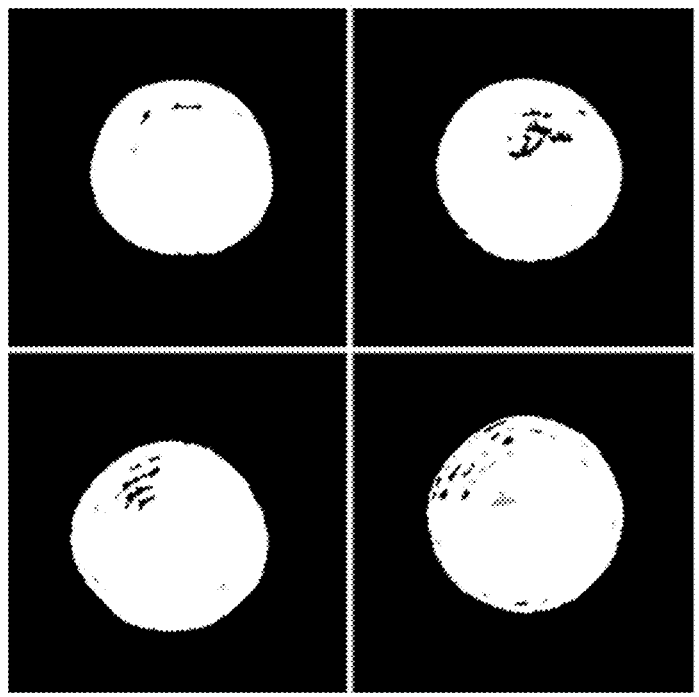
FIG. 30 shows bruise damage features as determined by a weighted damaged area function. Black-colored features have a higher likelihood of being associated with bruise damage, whereas gray-colored areas are considered somewhat less likely to be part of a bruise. Onion dropped six times from 17.5 cm. Two high likelihood bruise features and two intermediate likelihood features remain after analysis. Top Right: Onion dropped six times from 35 cm. Only high likelihood features remain. Bottom Left: Onion that was dropped twice from 70 cm. The largest, concentric features all rank as high likelihood bruise features. Bottom Right: Most spurious features have been excluded, though a few intermediate likelihood bruise features and one high likelihood feature remain around the periphery of the bulb.

Damage features were easily isolated via a manual bilevel image value segmentation. However, this technique has drawbacks; hollow center shoots in the onions were often included in the segmented features, as were normal minor blemishes and some particularly dark inter-scale spaces. FIG. 29 shows transverse cross sectional images after manual removal of the specimen holder in the image and bilevel segmentation. In all specimens, with the exception of the one dropped from 35 cm, hollow bulb centers have been segmented along with bruise damage. The segmented image of the bulb dropped from 105 cm showed spurious dark regions in the bulb's tissue that were segmented along with the damage features.

Figure 31:
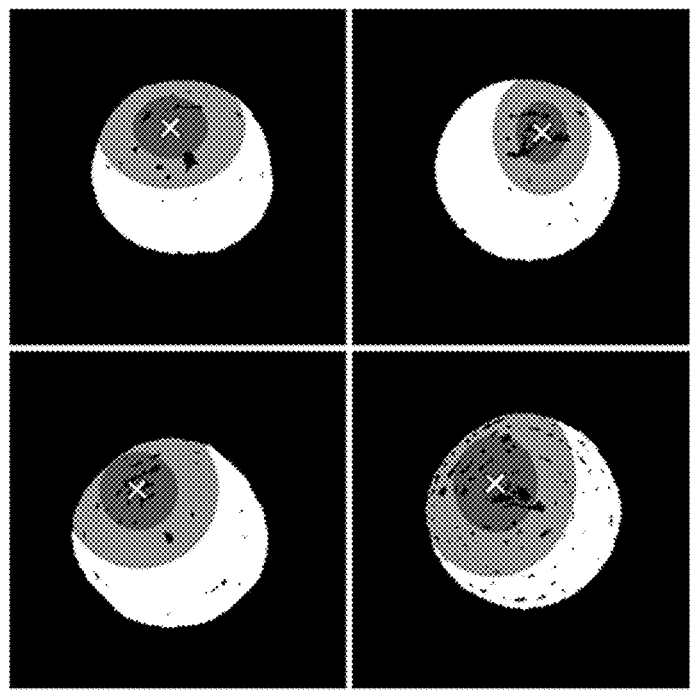
FIG. 31 shows localization of damage features in the onion cross section images. White crosses indicate the predicted center of damage based on the arrangement of detected damage features. Dark gray shaded regions indicate a neighborhood within one standard deviation from the predicted center, and light gray regions indicate areas within two standard deviations of the center. Such statistical means are useful in screening features caused by mechanical damage to onion bulbs from other low density features in onion tissues that could be caused by natural morphological variation, uneven drying, or pathogen damage.
Figure 32:
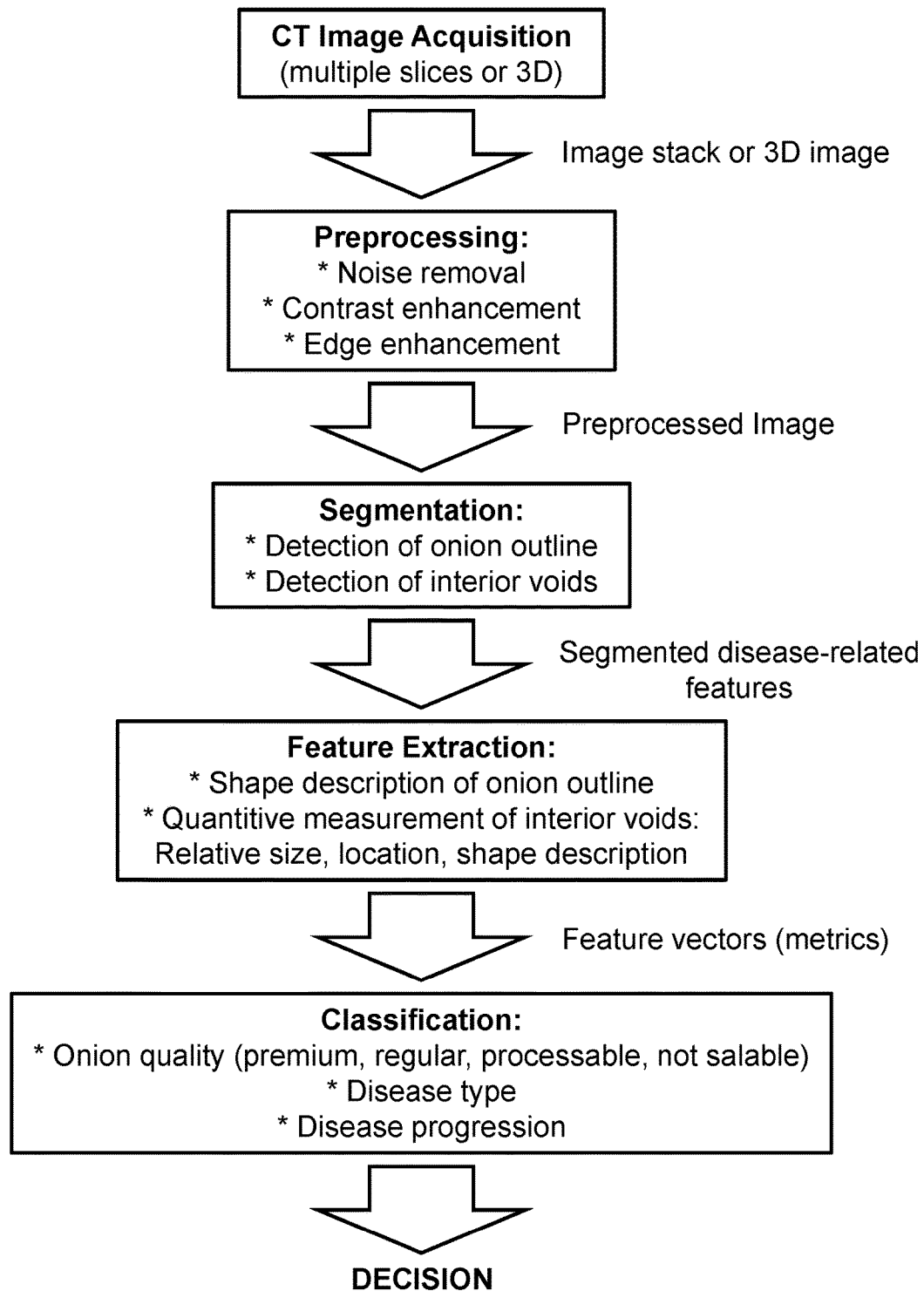
FIG. 32 is a flow-diagram illustrating the method of assessing an onion bulb for quality and marketability according to the methods of the disclosure.

Both evaluation techniques discriminate bruise damage features from other low density regions inside onion tissues. The results of the scaled damaged area calculation that is based on a feature's distance from the onion centroid can be seen in FIG. 30. Threshold values that determine whether a feature is considered part of a bruise were arbitrarily chosen. In FIG. 31 gray-colored features have values between 5 and 10. Black-colored features have values of 10 and above. In practice, this weighted damaged area should be normalized, and threshold values would be between 0 and 1, thereby allowing for a wide range of different size onions to be evaluated. The higher the weighted damaged area value of a feature, the more likely this feature is to be part of a bruise.

FIG. 31 shows the calculated center of bruise damage for each specimen and an associated neighborhood surrounding this center. If there are several large pixel area regions that fall outside this central neighborhood, it can be an indication of widespread pathogen damage. Smaller features located outside this neighborhood, by contrast, can simply be vascular structures in the onion tissues that were included in the damage feature segmentation process.

FIG. 31 shows localization of damage features in the onion cross section images. White crosses indicate the predicted center of damage based on the arrangement of detected damage features. Dark gray shaded regions indicate a neighborhood within one standard deviation from the predicted center, and light gray regions indicate areas within two standard deviations of the center. Such statistical means are useful in screening features caused by mechanical damage to onion bulbs from other low density features in onion tissues that could be caused by natural morphological variation, uneven drying, or pathogen damage.

Example 6

Classification is a computer-driven process in which a number of descriptive metrics is used to provide a decision. Such a decision could, for example, divide onions into groups with and without bacterial rot, or a ranking into groups of premium quality, regular quality, reduced quality (for immediate processing) and not salable. The metrics used for the classification (often referred to as the feature vector) are a number of quantitative values that describe a feature of interest. In the case of onions with suspected bacterial rot, such quantitative values could, for example, be the number, relative size, and distance from center of void spaces that are caused by shriveling layers. The task for the classifier is to distinguish feature vectors typical for intact onions from those with certain types of bacterial disease.

The input values that the classifier uses need to be distinctly different between healthy and diseased onions. One example is the Fourier descriptors of the outline. In onions with bacterial rot, Fourier coefficients of higher order increase in magnitude relative to the first Fourier coefficient. The relative aspect of these descriptors is crucial. For example, the magnitude of the first Fourier coefficient describes onion size. Higher-order Fourier coefficients also scale with size, but the ratio of any higher-order Fourier coefficient to the first Fourier coefficient describes the irregularity of the outline independent of size. Only the latter can serve as a shape-descriptive metric.

Several classifiers are available to provide a decision based on a feature vector. In its simplest form, classification can be performed with a decision tree. The decision tree acts like a flow diagram of consecutive questions: Is the second normalized Fourier descriptor greater than X? If no, healthy onion.

If yes—are there multiple void regions with a total relative size greater than Y? If no, healthy onion. If yes, are these void regions closer to the perimeter in average than to the center? If yes . . . etc. The decision tree is a good illustrative example of how the values of a feature vector lead to an eventual decision. Its downside is its relative inflexibility.

Classifiers more suitable for the task at hand are clustering techniques (e.g., k-means clustering or fuzzy c-means clustering), whereby the n-dimensional feature vectors of the individual onions form "point clouds" in n-dimensional space. If we claim, for example, that there are three groups (healthy, *botrytis*, sourskin), the point cloud can be subdivided into three subgroups, and each individual point assigned to one of the classes based on a minimum-squared-distance criterion.

Commonly used classifiers are also artificial neural networks and genetic algorithms. For these to work, a training set of feature vectors needs to be provided. The algorithms "learn" from the training set by adjusting internal weight parameters. After the learning period, the classifier's output takes feature vectors and classifies them according to the learned data.

REFERENCES

[1] E. G. Barcelon, S. Tojo, and K. Watanabe. X-ray computed tomography for internal quality evaluation of peaches. *Journal of Agricultural Engineering Research*, 73:323-330, 1999.

[2] E. G. Barcelon, S. Tojo, and K. Watanabe. Relating X-ray absorption and some quality characteristics of mango fruit (*Mangifera indica* L.). *Journal of Agriculture and Food Chemistry*, 47:3822-3825, 1999.

[3] P. Bertolini and S. P. Tian. Effect of temperature of production of *Botrytis allii* conidia on their pathogenicity to harvested white onion bulbs. *Plant Pathology*, 46(3): 432-438, 1997.

[4] G. E. Boyhan and W. T. Kelley. 2007 Onion production guide, January 2007. URL http://www.caes.uga.edu/applications/publications/files/pdf/Br/0201198\-2\_2.PDF. Accessed Oct. 22, 2012.

[5] G. E. Boyhan and R. L. Torrance. Vidalia sweet onions sweet onion production in southeastern Georgia. *Hort Technology*, 12(2):196-202, 2002.

[6] G. E. Boyhan, A. C. Purvis, W. M. Randle, R. L. Torrance, M. J. C. IV, G. Hardison, R. H. Blackley, H. Paradice, C. R. Hill, and J. T. Paulk. Harvest and postharvest quality of short-day onions in variety trials in Georgia, 2000-03. *Hort Technology*, 15 (3):694-706, July-September 2005.

[7] J. K. Brecht, R. L. Shewfelt, J. C. Garner, and E. Tollner. Using X-ray computed tomography to nondestructively determine maturity of green tomatoes. *HortScience*, 26(1):45, 1991.

[8] J. Brewster. Biochemistry, health benefits, and food science of alliums. In J. Brewster, editor, *Onions and Other Vegetable Alliums*, 2nd Edition, Crop Production Science in Horticulture, chapter 8, pages 347-372. CABI Publishing, 2008.

[9] J. Brewster. The classification, origins, distribution and economic importance of the major vegetable crops. In J. Brewster, editor, *Onions and Other Vegetable Alliums*, Crop Production Science in Horticulture, chapter 1, pages 1-26. CABI Publishing, 2 edition, 2008.

[10] W. H. Burkholder. Sour skin, a bacterial rot of onion bulbs. *Phytopathology*, 40(1): 115-117, 1950.

[11] M. I. Chilvers and L. J. du Toit. Detection and identification of *botrytis* species associated with neck rot, scape blight, and umbel blight of onion. Plant Health Progress, November 2006. URL http://onion.coop/wp-content/uploads/2011/11/Onion-Botrytis-Diagnostic-Guide-PHP-Nov-2006.pdf. Accessed Oct. 8, 2012.

[12] J. C. Diaz-Perez, A. C. Purvis, and J. T. Paulk. Bolting, yield, and bulb decay of sweet onion as affected by Nitrogen fertilizer. *Journal of the American Society of Horticultural Science*, 128(1):144-149, 2003.

[13] I. R. Donis-Gonzalez, D. E. Guyer, and A. Pease. Application of response surface methodology to systematically optimize image quality in computer tomography: A case study using fresh chestnuts (*Castanea* spp.). *Computers and Electronics in Agriculture*, 87:94-107, 2012.

[14] L. J. du Toit and M. L. Deerie. Prevalence of *Botrytis* spp. in onion seed crops in the Columbia basin of Washington. *Plant Disease*, 88(10):1061-1068, October 2004.

[15] Food and Agriculture Organization of the United Nations. FAOSTAT crop production statistics, August 2012. URL site/567/DesktopDefaultaspx?PageID=567. Accessed Sep. 23, 2012.

[16] J. H. Fromm, I. Sautter, D. Matthies, J. Kremer, P. Schumacher, and C. Ganter. Xylem water content and wood density in spruce and oak trees detected by high-resolution computed tomography. *Plant Physiology*, 127 (2):416-425, October 2001.

[17] R. Gitaitis. Bacterial streak and bulb rot of sweet onion: II. Epiphytic survival of *Pseudomonas viridiflava* in association with multiple weed hosts. *Plant Disease*, 82(8), 1998.

[18] R. Gitaitis, R. Baird, R. Weaver, and D. Sumner. Bacterial blight of sweet onion caused by *Pseudomonas viridiflava* in Vidalia, Ga. *Plant Disease*, 75(11):1180-1182, 1991.

[19] I. Gubb and H. MacTavish. Onion pre- and postharvest considerations. In H. Rabinowitch and L. Currah, editors, *Allium* Crop Science: Recent Advances, chapter 10, pages 233-266. CABI Publishing, 2002.

[20] M. A. Haidekker. Image analysis and visualization software. In *Advanced Biomedical Image Analysis*, chapter 14, pages 441-474. John Wiley and Sons, Hoboken, 2011.

[21] M. A. Haidekker. Shape analysis. In *Advanced Biomedical Image Analysis*, chapter 9, pages 276-309. John Wiley and Sons, Hoboken, 2011.

[22] M. A. Haidekker. Computed tomography. In *Medical Imaging Technology*, chapter 3, pages 37-54. Springer, New York, 2013.

[23] M. A. Haidekker. X-ray projection imaging. In *Medical Imaging Technology*, chapter 2, pages 13-36. Springer, New York, 2013.

[24] B. Herold, B. Oberbarnscheidt, and M. Geyer. Mechanical load and its effect on bulb onions due to harvest and post-harvest handling. *Journal of Agricultural Engineering Research*, 71:373-383, 1998.

[25] J. Lammertyn, T. Dresselaers, P. V. Hecke, P. Jancsok, M. Wevers, and B. Nicolai. MRI and CT study of spatial distribution of core breakdown in 'Conference' pears. *Magnetic Resonance Imaging*, 21:805-815, 2003.

[26] J. H. Leitao, S. A. Sousa, A. S. Ferreira, C. G. Ramos, I. N. Silva, and L. M. Moreira. Pathogenicity, virulence factors, and strategies to fight against *Burkholderia cepacia* complex pathogens and related species. *Applied Microbiology and Biotechnology*, 87(1): 31-40, 2010.

[27] C. Li, N. E. Schmidt, and R. D. Gitaitis. Detection of onion postharvest diseases by analyses of headspace volatiles using a gas sensor array and GC-MS. *LWT— Food Science and Technology*, 44:1019-1025, 2011.

[28] E. Mahenthiralingam, A. Baldwin, and C. Dowson. *Burkholderia cepacia* complex bacteria: opportunistic pathogens with important natural biology. *Journal of Applied Microbiology*, 104:1539-1551, 2008.

[29] G. Mark, R. Gitaitis, and J. Lorbeer. Bacterial diseases of onion. In H. Rabinowitch and L. Currah, editors, *Allium Crop Science: Recent Advances*, chapter 11, pages 267-292. CABI Publishing, 2002.

[30] B. W. Maw and B. G. Mullinix. Moisture loss of sweet onions during curing. *Postharvest biology and technology*, 35:223-227, 2005.

[31] B. W. Maw, Y. Hung, E. W. Tollner, D. A. Smittle, and B. G. Mullinix. Detecting impact damage of sweet onions using muriatic acid and X-rays. *Applied Engineering in Agriculture*, 11(6):823-826, 1995.

[32] B. W. Maw, D. A. Smittle, and B. G. Mullinix. The influence of harvest maturity, curing and storage conditions upon the storability of sweet onions. *Applied Engineering in Agriculture,* 13(4):511-515, 1997.

[33] B. W. Maw, D. A. Smittle, B. G. Mullinix, and J. S. Cundiff. Design and evaluation principles for mechanically harvesting sweet onions. *Transactions of the ASAE,* 41(3): 517-524, 1998.

[34] I. Meglinski, C. Buranachai, and L. Terry. Plant photonics: Application of optical coherence tomography to monitor defects and rots in onion. *Laser Physics Letters,* 7 (4):307-310, 2010.

[35] M. R. P. Mosqueda, E. W. Tollner, G. E. Boyhan, and R. W. McClendon. Predicting the economics of X-ray inspection technology in sweet onion packinghouses using simulation modelling. *Biosystems engineering,* 105 (1):139-147, 2010.

[36] G. Q. Pelter, R. Mittelstadt, B. G. Leib, and C. A. Redulla. Effects of water stress at specific growth stages on onion bulb yield and quality. *Agricultural Water Management,* 68(2):107-115, 2004.

[37] B. Prithiviraj, A. Vikram, A. Kushalappa, and V. Yaylayan. Volatile metabolite profiling of onion inoculated with *Erwinia carotovora* spp. *carotovora, Fusarium oxysporum* and *Botrytis allii. European Journal of Plant Pathology,* 110:371-377, 2004.

[38] A. Purvis and J. Brock. Does *Botrytis* allii spread from infected onions to sound onions in controlled atmosphere storage? In J. Oosterhaven and H. Peppelenbos, editors, *Proceedings of the* 8*th International Controlled Atmosphere Research Conference*, number 600 in Acta Horticulturae, page 615. International Society for Horticultural Science, March 2003.

[39] A. Purvis and A. Hakim. Effect of bruising on weight loss and storage quality of two onion cultivars. In 1998 *Georgia Onion Research-Extension Report*. University of Georgia College of Agricultural and Environmental Sciences, 1998. Cooperative Research-Extension Publication No. 3-99.

[40] H. F. Schwartz and S. K. Mohan. *Compendium of Onion and Garlic Diseases and Pests*. Disease compendium series of the American Phytopathological Association. APS Press, American Phytopathological Society, 2nd edition edition, 2008.

[41] M. A. Shahin, E. W. Tollner, R. D. Gitaitis, D. R. Sumner, and B. W. Maw. Classification of sweet onions based on internal defects using image processing and neural network techniques. *Transactions of the ASAE,* 45(5):1613-1618, 2002.

[42] L. Shepp and B. Logan. The fourier reconstruction of a head section. *IEEE Trans Nucl. Sci,* 21(3):21-43, 1974.

[43] L. Sonego, R. Ben-Arie, J. Raynal, and J. Pech. Biochemical and physical evaluation of textural characteristics of nectarines exhibiting woolly breakdown: NMR imaging, X-ray computed tomography, and pectin composition. *Postharvest Biology and Technology,* 5: 187-198, 1995.

[44] N. Syed, M. Munir, A. A. Alizai, and A. Ghaffoor. Onion yield and yield components as function of the levels of Nitrogen and Potassium application. *Pakistan Journal of Biological Sciences,* 3(12):2069-2071, 2000.

[45] E. W. Tollner. Efficacy and economics of placing X-ray machines in an onion packing-house. *Recent Research Developments in Crop Science,* 1:55-69, 2004.

[46] E. W. Tollner, R. D. Gitaitis, K. W. Seebold, and B. W. Maw. Experiences with a food product X-ray inspection system for classifying onions. *Applied Engineering in Agriculture,* 21(5):907-912, 2005.

[47] E. W. Tollner, S. E. Prussia, and W. J. Florkowski. Modeling product flow through a generic postharvest distribution system. *Journal of Food Distribution Research,* 37(2): 23-34, 2006.

[48] United States Department of Agriculture. U.S. onion statistics (94013), 2010. URL usda.mannlib.cornell.edu/MannUsda/viewDocumentInfo.do?documentID=1396. Accessed Sep. 23, 2012.

[49] University of Georgia College of Agricultural and Environmental Sciences Center for Agribusiness Economic Development. Georgia farm gate value report, 2002. URL http://www.caes.uga.edu/center/caed/pubs/2003/documents/AR-03-01.pdf. Accessed May 10, 2012.

[50] University of Georgia College of Agricultural and Environmental Sciences Center for Agribusiness Economic Development. Georgia farm gate value report, 2010. URL http://www.caes.uga.edu/center/caed/pubs/2011/documents/AR-11-01.pdf. Accessed May 10, 2012.

[51] A. Vikram, H. Hamzehzarghani, and A. Kushalappa. Volatile metabolites from the headspace of onion bulbs inoculated with postharvest pathogens as a tool for disease discrimination. *Canadian Journal of Plant Pathology,* 27:194-203, 2005.

[52] W. Wang, C. Li, E. W. Tollner, R. D. Gitaitis, and G. C. Rains. Shortwave infrared hyperspectral imaging for detecting sour skin (*Burkholderia cepacia*)-infected onions. *Journal of Food Engineering,* 109(1):38-48, 2012.

[53] P. J. Wright and C. M. Triggs. Effects of curing, moisture, leaf removal, and artificial inoculation with soft-rotting bacteria on the incidence of bacterial soft rot of onion (*Allium cepa*) bulbs in storage. *Australian Plant Pathology,* 34(1):355-359, 2005.

[54] D. S. Yohalem, K. Nielsen, and M. Nicolaisen. Taxonomic and nomenclatural clarification of the onion neck rotting *botrytis* species. *Mycotaxon,* 85:175-182, 2003.

The invention claimed is:

1. A non-transitory computer-readable medium embodying a program executable in at least one computing device, comprising code that:
   accesses a computed tomography (CT) image of an onion bulb;
   processes the image of the CT image to adjust a quality of the CT image;
   identifies an outline of the onion bulb in the CT image;
   identifies a plurality of interior voids of the onion bulb;
   generates a shape description of the onion bulb based at least in part on the plurality of interior voids, the outline of the onion bulb, or a combination thereof;
   generates a plurality of measurements for the interior voids of the onion bulb; and
   generates a classification for the onion bulb describing a condition of the onion bulb based at least in part on the plurality of measurements, the shape description, or a combination thereof, wherein performing image processing further comprises generating a modified image of the onion bulb comprising only the plurality of interior voids of the onion bulb, wherein the classification is generated based at least in part on the modified image.

2. A system, comprising:
   at least one computing device; and
   an onion classification application executed in the at least one computing device, the onion classification application comprising logic that:

accesses a computed tomography (CT) image of an onion bulb;
processes of the CT image to adjust a quality of the CT image;
identifies an outline of the onion bulb in the CT image;
identifies a plurality of interior voids of the onion bulb;
generates a shape description of the onion bulb based at least in part on the plurality of interior voids, the outline of the onion bulb, or a combination thereof;
generates a plurality of measurements for the interior voids of the onion bulb; and
generates a classification for the onion bulb describing a condition of the onion bulb based at least in part on the plurality of measurements, the shape description, or a combination thereof, wherein performing image processing further comprises generating a modified image of the onion bulb comprising only the plurality of interior voids of the onion bulb, wherein the classification is generated based at least in part on the modified image.

3. A computer-implemented method, comprising:
accessing, by at least one computing device comprising at least one hardware processor, a computed tomography (CT) image of an onion bulb;
performing, by the at least one computing device, image processing of the CT image to adjust a quality of the CT image;
identifying, by the at least one computing device, an outline of the onion bulb in the CT image;
identifying, by the at least one computing device, a plurality of interior voids of the onion bulb;
generating, by the at least one computing device, a shape description of the onion bulb based at least in part on the plurality of interior voids, the outline of the onion bulb, or a combination thereof;
generating, by the at least one computing device, a plurality of measurements for the interior voids of the onion bulb; and
generating, by the at least one computing device, a classification for the onion bulb describing a condition of the onion bulb based at least in part on the plurality of measurements, the shape description, or a combination thereof, and wherein performing image processing further comprises generating, by the at least one computing device, a modified image of the onion bulb comprising only the plurality of interior voids of the onion bulb, wherein the classification is generated based at least in part on the modified image.

* * * * *